(12) United States Patent
Kimoto et al.

(10) Patent No.: US 7,250,278 B2
(45) Date of Patent: Jul. 31, 2007

(54) α-KETO ACID REDUCTASE, METHOD FOR PRODUCING THE SAME, AND METHOD FOR PRODUCING OPTICALLY ACTIVE α-HYDROXY ACIDS USING THE SAME

(75) Inventors: Norihiro Kimoto, Ibaraki (JP); Hiroaki Yamamoto, Ibaraki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 475 days.

(21) Appl. No.: 10/619,779

(22) Filed: Jul. 15, 2003

(65) Prior Publication Data
US 2004/0086993 A1  May 6, 2004

(30) Foreign Application Priority Data
Jul. 16, 2002  (JP) ............................. 2002-207507

(51) Int. Cl.
C12N 9/02   (2006.01)
C12N 1/20   (2006.01)
C12N 15/00  (2006.01)
C12Q 1/26   (2006.01)
C12P 21/04  (2006.01)
C07H 21/04  (2006.01)

(52) U.S. Cl. .................... 435/189; 435/440; 435/252.3; 435/320.1; 435/69.1; 435/71.1; 435/25; 536/23.7; 536/23.2

(58) Field of Classification Search ................. 435/189, 435/252.3, 320.1, 69.1, 71.1, 18, 25, 440; 536/23.2, 23.7, 23.1; 530/350
See application file for complete search history.

(56) References Cited

U.S. PATENT DOCUMENTS 4,609,623 A *  9/1986  Leuchtenberger et al. .. 435/130

2003/0119173 A1  6/2003  Mitsuhashi et al. ......... 435/280

FOREIGN PATENT DOCUMENTS

EP        0527553       2/1993

(Continued)

OTHER PUBLICATIONS

Bolotin et al. The complete genome sequence of the lactic acid bacterium *Lactococcus lactis* ssp. lactis IL1403.☐☐Genome Res. May 2001;11(5):731-53.*

(Continued)

*Primary Examiner*—P. Achutamurthy
*Assistant Examiner*—Yong D. Pak
(74) *Attorney, Agent, or Firm*—Lahive & Cockfield, LLP; Jeanne M. DiGiorgio

(57) ABSTRACT

The present invention provides an α-keto acid reductase isolated from *Leuconostoc mesenteroides* subsp. *dextranicum*, and a DNA encoding the reductase. The enzyme and homologs thereof reduce α-keto acids under the presence of NADH to produce optically active α-hydroxy acids. The α-hydroxy acids of the present invention include optically active mandelic acid derivatives of formula II. The optically active mandelic acid derivatives obtained by the present invention are useful as intermediates in synthesizing pharmaceuticals and pesticides

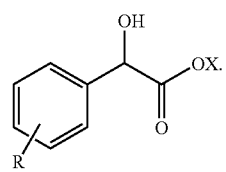

formula (II)

6 Claims, 9 Drawing Sheets

FOREIGN PATENT DOCUMENTS

| | | |
|---|---|---|
| JP | 57-198096 | 12/1982 |
| JP | 57-198097 | 12/1982 |
| JP | 63-032492 | 2/1988 |
| JP | 06-007179 | 1/1994 |
| JP | 2001-072644 | 3/2001 |

OTHER PUBLICATIONS

Bolotin et al.—Sequence Alignment.*

Taxonomy brower (Leuconostoc mesenteroides subsp. dextranicum).*

EMBL Acc. No. AE008817; *Salmonella typhimurium* LT2, section 121 of 220 of the complete genome.

EMBL Acc. No. AF454824; *Enterococcus faecalis* pathogenicity island, complete sequence.

Kallwass "Potential of *R*-2-hydroxyisocaproate dehydrogenase from *Lactobacillus casei* for stereospecific reductions." *Enzyme Microb. Technol.* 1992;14:28-35.

Zheng et al. "Kinetic and mechanistic analysis of the *E. coli* panE-encoded ketopantoate reductase." *Biochemistry*. Apr. 4, 2000;39(13):3708-17.

EMBL Acc. No. AE008817; *Salmonella typhimurium* LT2, section 121 of 220 of the complete genome, 2001.

EMBL Acc. No. AF454824; *Enterococcus faecalis* pathogenicity island, complete sequence, 2002.

GenBank Accession No. Q8Z4L0, Parkhill, J. et al., "Complete genome sequence of a multiple drug resistant Salmonella enterica serovar Typhi CT18," *Nature,* vol. 413(6858);848-852 (2001).

* cited by examiner ic reduction are known. However, substrates that can be used in these methods are limited to phenylglyoxylic acid that has no substituent on the benzene ring. No method for producing an optically active mandelic acid that has substituents on the benzene ring by microorganism-mediated asymmetric reduction of a phenylglyoxylic acid derivative is known in the art.

α-KETO ACID REDUCTASE, METHOD FOR PRODUCING THE SAME, AND METHOD FOR PRODUCING OPTICALLY ACTIVE α-HYDROXY ACIDS USING THE SAME

RELATED APPLICATIONS

This application claims priority to the Japanese Patent Application Serial No. 2002-207507 JP filed on Jul. 16, 2002, the entire contents of which is hereby expressly incorporated herein by reference.

FIELD OF THE INVENTION

The present invention relates to a novel reduced β-nicotinamide adenine dinucleotide-dependent α-keto acid reductase. The present invention also relates to polynucleotides encoding the reductase, method for producing the reductase, and a method for producing optically active α-hydroxy acids, in particular, (R)-2-chloromandelic acid, using a recombinant that expresses the reductase.

BACKGROUND OF THE INVENTION

In general, enzymes not only have high catalytic activity but also exhibit stereospecificity, substrate specificity and reaction specificity. The stereospecificity of an enzyme is almost absolute with some exceptions.

According to recent research, the importance of the use of optically active substances in the field of pharmaceuticals, pesticides, animal foods, spices, etc. is increasing. Specifically, optical isomers sometimes have completely different physiological activities to each other, and thus techniques to specifically obtain optical isomers are important. For example, when only one of two enantiomers has the physiological activity of interest, the problem of a mixture of the enantiomers is not only that the other isomer has no activity in the mixture but also may competitively inhibit the coexisting effective enantiomer. Because of such competition, the biological activity of a racemate may be greatly decreased up to ½ as compared with that of the effective enantiomer. Therefore, it is an industrially important objective to develop methods for obtaining optically pure enantiomers (synthesis or resolution).

A technique widely used to achieve the objective comprises the synthesis of racemate followed by effective optical resolution of the synthesized racemate. However, according to this technique comprising the optical resolution after synthesis, an unintended enantiomer is always synthesized as a by-product. Thus, this technique is still problematic with respect to efficient utilization of raw materials. Even when the recovered by-product is regenerated as the raw material, a constant amount of by-product is always repeatedly synthesized. Hence, an enzymatic optical resolution method that neither produces a by-product nor produces a large volume of waste liquid has been attracting attention. The enzymatic optical resolution method utilizes specific generation of an objective enantiomer by taking advantage of the specificity of enzymes. This method suppresses the synthesis of unnecessary enantiomer so that they are produced at low levels. As a result of this method, products with high optical purity can be readily obtained. In addition, this method is advantageous for its efficient use of raw materials.

Optically active α-hydroxy acids include optically active mandelic acid, which is useful as an intermediate for synthesizing pharmaceuticals and pesticides. Known methods for producing optically active mandelic acid having a substituent on the benzene ring include the following:

optical resolution method comprising fractional crystallization of racemates (Unexamined Published Japanese Patent Application No. (JP-A) 2001-72644);

chromatographic optical resolution (Journal of Chromatography, 282, 83–8, (1983));

method using nitrilase (JP-A Hei 4-99496; JP-A Hei 6-237789);

method for obtaining an optical isomer by oxidizing one of the isomer in a racemate (JP-A Hei 6-165695); and method using hydroxylnitrile lyase (JP-A 2001-354616).

The method using nitrilase requires a mandelonitrile derivative as the raw material. Sodium cyanide is necessary for the synthesis of the mandelonitrile derivative.

On the other hand, the method using hydroxylnitrile lyase requires benzaldehyde and hydrocyanic acid as the raw material. Due to its toxicity, hydrocyanic acid must be handled carefully.

A method for producing optically active mandelic acid by microorganism-mediated asymmetric reduction of phenylglyoxylic acid having no substituent on the benzene ring, is known in the art (JP-A Sho 57-198096; JP-A Sho 57-198097; JP-A Sho 63-32492; JP-A Hei 6-7179, etc.).

Methods for obtaining optical active substances of mandelic acid derivatives that have substituents on the benzene ring through enzymatic reactions will be of great use. However, no enzymatic method practicable on an industrial scale is known in the art.

SUMMARY OF THE INVENTION

An objective of the present invention is to provide an enzymatic method for producing an optically active α-hydroxy acid that has substituents on its benzene ring.

Another objective of the present invention is to provide a novel enzyme that generates an α-hydroxy acid with a high optical purity through the reduction of an α-keto acid using reduced β-nicotinamide adenine dinucleotide (hereinafter abbreviated as NADH) as a coenzyme. Another objective of the present invention is to isolate a DNA encoding an enzyme having the properties of interest as a recombinant. Furthermore, another objective of the present invention is to provide a method for producing optically active α-hydroxy acids using the recombinant.

The present inventors revealed that *Leuconostoc mesenteroides* subsp. *dextranicum* stereoselectively reduces 2-chlorophenyl glyoxylic acid to produce (R)-2-chloromandelic acid. Both the yield and stereoselectivity of this reaction were high.

The present inventors purified an enzyme that reduced 2-chlorophenyl glyoxylic acid from cell-free extract of the strain till the enzyme appeared as a single band via electrophoresis. The inventors also determined various properties of this enzyme. As a result, the inventors discovered that the enzyme is a novel α-keto acid reductase that reduces various types of α-keto acids. In a reduction reaction, the enzyme reduced 2-chlorophenyl glyoxylic acid to produce (R)-2-chloromandelic acid at a high yield and with a high optical purity. Furthermore, the inventors isolated a DNA encoding this enzyme and obtained a transformant expressing the enzyme at a high level. This transformant was confirmed to be useful for enzymatic production of optically active α-hydroxy acids, thereby allowing the successful completion of the present invention.

As described above, methods for producing optically active mandelic acid by microorganism-mediated asymmetric reduction of phenylglyoxylic acid that has no substituent on the benzene ring are known in the art. However, typically, it is difficult to assume that the same microorganism catalyzes a similar reaction using, as the substrate, a phenylglyoxylic acid having substituents on the benzene ring. The progress of a similar reaction cannot be expected due to the steric hindrance by the substituents, toxicity of the substrate compound or product to the microorganism, and difference in the electronic effect of the substrate depending on the substituents.

For example, as shown in the Examples described ahead, *Candida famata* IFO 0856 (JP-A Hei 6-7179) that reacts on phenylglyoxylic acid derivatives without substituent did not react on 2-chlorophenyl glyoxylic acid having the formula (I). This finding was surprising, since this compound of formula (I) has a Cl substitution at the ortho position of the benzene ring constituting the phenylglyoxylic acid derivative. More surprisingly, the optical purity of the optically active mandelic acid produced by the microorganism was very high sufficient for practical use.

Hitherto, known enzymes having the activity to NADH-dependently reduce α-keto acids include D-lactate dehydrogenase (D-LDH), D-α-hydroxyisocaproic acid dehydrogenase (D-HicDH), and D-mandelic acid dehydrogenase (D-ManDH) highly purified from lactic acid bacteria etc., and various properties thereof have been clarified (Enzyme Microb. Technol., 14, 28–35 (1992); Appl. Environ. Microbiol., 68, 2, 947–951 (2002)). However, all of these dehydrogenases show a dehydrogenating activity on α-hydroxy acids corresponding to the (α-keto acids. Hence, it appears that these known enzymes have different properties as compared to the α-keto acid reductase of the present invention.

Specifically, the present invention relates to an α-keto acid reductase, a DNA encoding the reductase, a method for producing the reductase, uses thereof, and a method for producing α-hydroxy acids (described below).

(1) An α-keto acid reductase having the following physicochemical properties:
  (i) function:
    reduces α-keto acid to produce (R)-α-hydroxy acid using reduced β-nicotinamide adenine dinucleotide as the coenzyme; and
  (ii) substrate specificity:
    (a) utilizes reduced β-nicotinamide adenine dinucleotide as the coenzyme in the reduction reaction of (i);
    (b) reducing 2-chlorophenyl glyoxylic acid to produce (R)-2-chloromandelic acid; and
    (c) reduces 2-chlorophenyl glyoxylic acid but substantially fails to dehydrogenate either of the two optical isomers of 2-chloromandelic acid;

(2) the α-keto acid reductase of (1), further having the following physicochemical properties:
  (iii) optimum pH:
    pH 5.0 to 5.5;
  (iv) optimum temperature:
    45 to 55° C.; and
  (v) molecular weight of about 35,000 Daltons and about 63,000 Daltons, as determined by sodium dodecyl sulfate-polyacrylamide gel electrophoresis and gel filtration, respectively;

(3) the α-keto acid reductase of (1), which is produced by a microorganism belonging to the genus *Leuconostoc*;

(4) the α-keto acid reductase of (3), wherein the microorganism belonging to the genus *Leuconostoc* is *Leuconostoc mesenteroides*;

(5) the α-keto acid reductase of (4), wherein the microorganism belonging to *Leuconostoc mesenteroides* is *Leuconostoc mesenteroides* subsp. *dextranicum*;

(6) a polynucleotide encoding a protein, wherein said protein is an enzyme that catalyzes the reduction of α-keto acids, and wherein said polynucleotide is selected from the group consisting of:
  (a) a polynucleotide comprising the nucleotide sequence of SEQ ID NO: 1;
  (b) a polynucleotide encoding a protein comprising the amino acid sequence of SEQ ID NO: 2;
  (c) a polynucleotide encoding a protein comprising the amino acid sequence of SEQ ID NO: 2, wherein one or more amino acids have been substituted, deleted, inserted, and/or added;
  (d) a polynucleotide hybridizing under stringent conditions to a DNA comprising the nucleotide sequence of SEQ ID NO: 1; and
  (e) a polynucleotide encoding an amino acid sequence which exhibits 50% or higher homology to the amino acid sequence of SEQ ID NO: 2;

(7) a protein encoded by the polynucleotide of (6);

(8) a recombinant vector wherein the polynucleotide of (6) has been inserted;

(9) the recombinant vector of (8), wherein a polynucleotide encoding a dehydrogenase catalyzing an oxidation-reduction reaction using β-nicotinamide adenine dinucleotide as the coenzyme has been further inserted;

(10) the vector of (9), wherein the dehydrogenase is a formate dehydrogenase;

(11) the vector of (10), wherein the formate dehydrogenase is derived from *Mycobacterium vaccae*;

(12) the vector of (9), wherein the dehydrogenase is a glucose dehydrogenase;

(13) the recombinant vector of (12), wherein the glucose dehydrogenase is derived from *Bacillus subtilis*;

(14) a transformant comprising any one of the polynucleotides of (6), or the vector of (8) in an expressible manner;

(15) a method for producing the protein of (7), wherein said method comprises the steps of culturing the transformant of (14), and collecting the expressed product;

(16) a method for producing the enzyme of (1) or the protein of (7), wherein said method comprises the step of culturing a microorganism belonging to the genus *Leuconostoc* that produces the enzyme of (1) or the protein of (7);

(17) the method of (16), wherein the microorganism belonging to the genus *Leuconostoc* is *Leuconostoc mesenteroides*;

(18) the method of (17), wherein the microorganism belonging to *Leuconostoc mesenteroides* is *Leuconostoc mesenteroides* subsp. *dextranicum*;

(19) a method for producing an optically active α-hydroxy acid, wherein said method comprises the following sequential steps:
  (i) reacting
    (a) the α-keto acid reductase of (1) or (2);
    (b) the protein of (7);
    (c) a microorganism producing said α-keto reductase or said protein; or
    (d) a processed product of the microorganism with an α-keto acid; and
  (ii) collecting the optically active α-hydroxy acid produced in step (i);

(20) the method of (19), wherein the α-keto acid is a phenylglyoxylic acid derivative of formula (I):

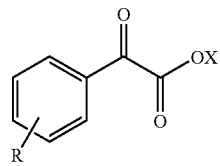

formula (I)

wherein:
X is a hydrogen atom, an alkaline metal, or a alkaline earth metal; and
R indicates one or more substituents at the ortho, meta, or para positions selected from the group consisting of a halogen atom, a hydroxyl group, a $C_{1-3}$ alkyl group, a $C_{1-3}$ alkoxy group, a $C_{1-3}$ thioalkyl group, an amino group, a nitro group, a mercapto group, a phenyl group, and a phenoxy group, and wherein said method comprises the step of collecting the optically produced active mandelic acid derivative of formula (II):

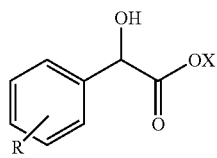

formula (II)

wherein X and R are as defined in Formula (I);

(21) the method of (20), wherein the ortho position of the phenylglyoxylic acid derivative is substituted;

(22) the method of (21), wherein the ortho position of the phenylglyoxylic acid derivative is substituted with a halogen atom;

(23) the method of (20), wherein the meta position of the phenylglyoxylic acid derivative is substituted;

(24) the method of (23), wherein the meta position of the phenylglyoxylic acid derivative is substituted with a halogen atom;

(25) the method of (19), wherein the α-keto acid is 2-chlorophenyl glyoxylic acid and the optically active α-hydroxy acid is (R)-2-chloromandelic acid;

(26) the method of (19), wherein the microorganism is the transformant of (14);

(27) the method of (19), wherein said method further comprises the step of converting oxidized β-nicotinamide adenine dinucleotide to reduced β-nicotinamide adenine dinucleotide;

(28) the method of (27), wherein the oxidized β-nicotinamide adenine dinucleotide is converted to reduced β-nicotinamide adenine dinucleotide by the function of an enzyme that catalyzes dehydrogenation using oxidized β-nicotinamide adenine dinucleotide as the coenzyme; and

(29) the method of (28), wherein the enzyme that catalyzes dehydrogenation using oxidized β-nicotinamide adenine dinucleotide as the coenzyme is formate dehydrogenase and/or glucose dehydrogenase.

DETAILED DESCRIPTION OF THE INVENTION

Figure 1:
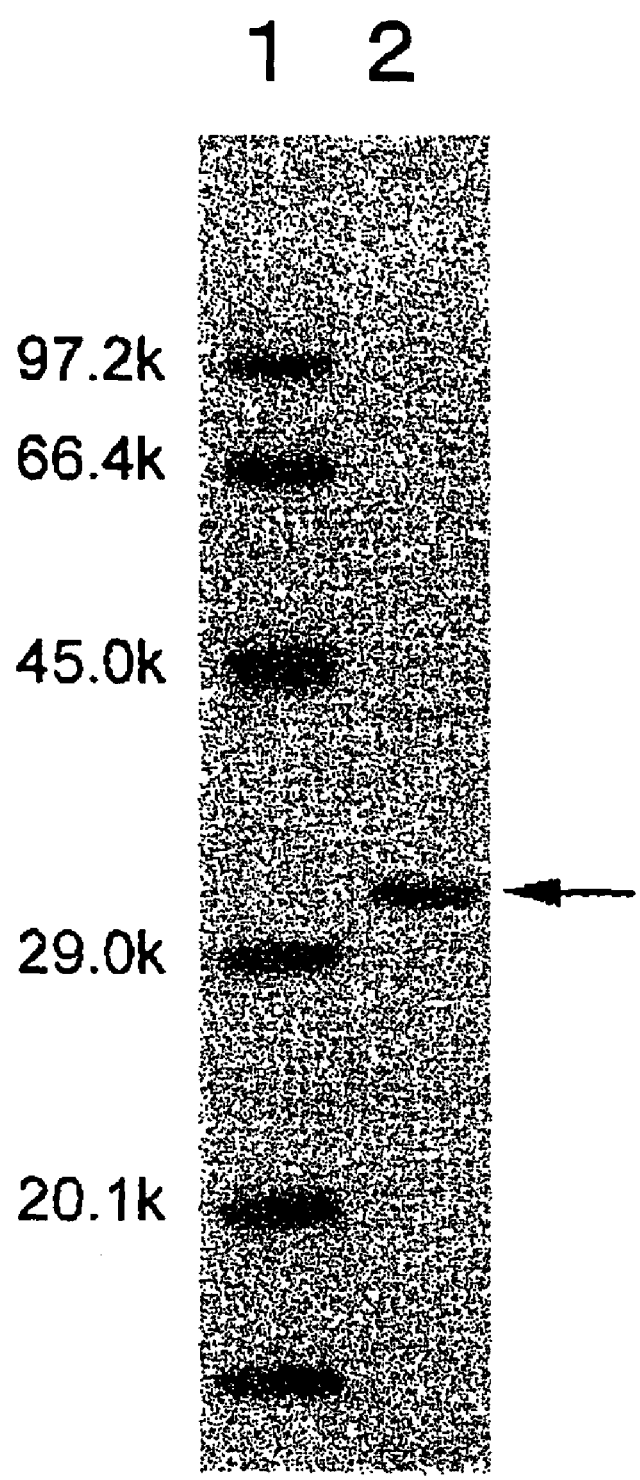
FIG. 1 shows a photograph depicting the electrophoretic pattern by SDS-PAGE. Lane 1, molecular weight marker; lane 2, the enzyme obtained in Example 1. The band indicated with an arrow corresponds to the enzyme.

The α-keto acid reductase of the present invention has the physicochemical properties of:
(i) function:
reduces α-keto acid to produce (R)-α-hydroxy acid using reduced β-nicotinamide adenine dinucleotide as the coenzyme; and
(ii) substrate specificity:
(a) utilizes reduced β-nicotinamide adenine dinucleotide as the coenzyme in the reduction reaction of (i);
(b) reducing 2-chlorophenyl glyoxylic acid to produce (R)-2-chloromandelic acid; and
(c) reduces 2-chlorophenyl glyoxylic acid but substantially fails to dehydrogenate either of the two optical isomers of 2-chloromandelic acid.

Preferably, the α-keto acid reductase of the present invention additionally has the physicochemical properties of:
(iii) optimum pH:
pH 5.0 to 5.5;
(iv) optimum temperature:
45 to 55° C.; and
(v) molecular weight of about 35,000 Daltons and about 63,000 Daltons, as determined by sodium dodecyl sulfate-polyacrylamide gel electrophoresis (hereinafter abbreviated as SDS-PAGE)and gel filtration, respectively.

An α-keto acid reductase of the present invention can be obtained, from *Leuconostoc mesenteroides* subsp. *dextranicum*. The α-keto acid reductase derived from the microorganism substantially cannot utilize reduced β-nicotinamide adenine dinucleotide phosphate (hereinafter abbreviated as NADPH) as the coenzyme. However, regardless of the ability to use NADPH, enzymes having the above-described physicochemical properties (i) and (ii) are encompassed in the α-keto acid reductase of the present invention. The α-keto acid reductase of the present invention preferably includes Enzymes additionally having the above-described properties (iii) to (v).

In the present invention, the dehydrogenase activity against 2-chloromandelic acid of an enzyme can be confirmed by the following assay procedure:incubate the enzyme at 30° C. in a reaction solution of 50 mM Tris-HCl buffer (pH 8.5) containing 2.5 mM NAD⁺, and 1 mM 2-chloromandelic acid; and measure the increase in absorbance at 340 nm associated with the generation of NADH. 1 U is defined as an amount of enzyme that catalyzes the production of 1 μmol NADH in one minute.

On the other hand, in the present invention, substantial absence of a dehydrogenase activity against both optical isomers of 2-chloromandelic acid of a certain protein can be determined by taking the activity of the protein to reduce 2-chlorophenyl glyoxylic acid as a relative activity of 100%, and confirming that the dehydrogenase activities of the protein against each of the two optical isomers of 2-chloromandelic acid is 20% or lower. Thus, "substantially fails to dehydrogenate either of the two optical isomers of 2-chloromandelic acid" indicates that the dehydrogenase activity of an enzyme against either of the two optical isomers of 2-chrolomandelic acid is 20% or lower taking the relative activity of the enzyme to reduce 2-chlorophenyl glyoxylic acid as 100%.

Furthermore, substantial inability of a certain protein to utilize NADPH can be determined by taking the activity of the protein to NADPH dependently reduce 2-chlorophenyl glyoxylic acid as a relative activity of 100%, and confirming that the NADPH-dependent 2-chlorophenyl glyoxylic acid-reducing activity of the protein is 20% or lower.

According to the present invention, an NADPH-dependent 2-chlorophenyl glyoxylic acid-reducing activity can be confirmed by the following assay procedure: incubate the enzyme at 30° C. in a reaction solution of 50 mM acetic acid-sodium acetate buffer (pH 5.5) containing 0.2 mM NADPH and 1 mM 2-chlorophenyl glyoxylic acid; and measuring a decrease in the absorbance at 340 nm associated with the decrease of NADPH. 1 U is defined as an amount of enzyme that catalyzes the decrease of 1 □mol NADPH in one minute.

Alternatively, a preferred α-keto acid reductase according to the present invention can be characterized by the properties of: (1) being capable to use NADH as a coenzyme; (2) substantial lack of dehydrogenase activity against α-hydroxy acids; and (3) reducing 2-chlorophenyl glyoxylic acid using NADH as the coenzyme to produce (R)-2-chloromandelic acid with an optical purity of 99% ee (enantiomeric excess) or higher.

An α-keto acid reductase having the above-described physicochemical properties can be purified, for example, from culture of a lactic acid bacterium belonging to the genus *Enterococcus, Lactobacillus*, or *Leuconostoc*. Microorganisms having particularly excellent productivity of α-keto acid reductase of the present invention include *Enterococcus faecalis* and *Enterococcus hirae* of the genus *Enterococcus; Lactobacillus fructivorans* and *Lactobacillus hilgardii* of the genus *Lactobacillus*; and *Leuconostoc mesenteroides* subsp. *dextranicum* of the genus *Leuconostoc*. Strains of *Leuconostoc mesenteroides* subsp. *dextranicum* that can be used to prepare the α-keto acid reductase of the present invention include ATCC 17072 and NRIC 1085.

An α-keto acid reductase of the present invention can be prepared as follows. First, the above microorganisms are cultured in a medium, such as MRS medium, generally used for culturing lactic acid bacteria. Then sufficiently grown cells of the microorganism are harvested, and a cell-free extract is prepared by lysing the cells in a buffer supplemented with a reducing agent (e.g., 2-mercaptoethanol) and a protease inhibitor (e.g., phenylmethanesulfonyl fluoride). The enzyme of interest can be purified from the cell-free extract by appropriate combination of fractionation based on protein solubility (precipitation using organic solvent; salting out with ammonium sulfate, etc.); cation-exchange chromatography; anion-exchange chromatography; gel filtration; hydrophobic chromatography; and affinity chromatography using chelating agent, dye, antibody, etc. For example, the enzyme of the present invention can be purified as a single band on electrophoresis with a series of procedures utilizing hydrophobic chromatography using phenyl-Sepharose, anion-exchange chromatography using Mono Q, hydrophobic chromatography using butyl-Sepharose, and adsorption chromatography with hydroxyapatite.

The present invention relates to polynucleotides encoding (α-keto acid reductase and homologs of the polynucleotides. In addition to natural polynucleotides such as DNA and RNA, a polynucleotide of the present invention may be an artificial molecule including artificial nucleotide derivatives. A polynucleotide of the present invention can also be a chimeric molecule of DNA-RNA. The polynucleotides of the present invention encoding α-keto acid reductase include the nucleotide sequence of SEQ ID NO: 1. The nucleotide sequence of SEQ ID NO: 1 encodes a protein comprising the amino acid sequence of SEQ ID NO: 2. The protein comprising the amino acid sequence is a preferable embodiment of the α-keto acid reductase of the present invention.

The homologs of polynucleotides encoding the α-keto acid reductase of the present invention include polynucleotides encoding a protein having the above-described physicochemical properties (i) and (ii), and which comprise the amino acid sequence of SEQ ID NO: 2 wherein one or more amino acids have been deleted, substituted, inserted, and/or added. One skilled in the art can obtain homologs of the polynucleotides of the present invention by appropriately introducing substitutions, deletions, insertions and/or additions into the polynucleotide of SEQ ID NO: 1 utilizing site-directed mutagenesis (Nucleic Acid Res., 10, 6487 (1982); Methods in Enzymol., 100, 448 (1983); "Molecular Cloning $2^{nd}$ Edition", Cold Spring Harbor Laboratory Press (1989); "PCR A Practical Approach", IRL Press, 200 (1991)), etc.

The homologs of a polynucleotide of the present invention also include polynucleotides hybridizing under stringent conditions to a polynucleotide that comprises the nucleotide sequence of SEQ ID NO: 1, and which encodes a protein having the above-described physicochemical properties (i) and (ii). The phrase a "polynucleotide hybridizing under stringent conditions" refers to a polynucleotide that hybridizes to one or more probe DNAs which comprises a sequence of at least 20, preferably at least 30 continuous residues (for example, 40, 60 or 100 continuous residues) arbitrary selected from the sequence of SEQ ID NO: 1, for example, using ECL direct nucleic acid labeling and detection system (Amersham Pharmacia Biotech) under the conditions described in the manual (washing at 42° C. in a primary wash buffer containing 0.5×SSC).

The homologs of the polynucleotides of the present invention also include polynucleotides encoding a protein having a homology of at least 50%, preferably at least 60%, and more preferably 70% or higher to the amino acid sequence of SEQ ID NO: 2. A preferred protein of the present invention comprises an amino acid sequence having a homology of 80% or higher, 85% or higher, preferably 90% or higher, and more preferably 95% or higher (for example, 98% or higher) to the amino acid sequence of SEQ ID NO: 2. A homology search of a protein can be carried out against databases of the amino acid sequence of proteins (e.g., SWISS-PROT and PIR), databases of DNA sequences (e.g., DDBJ, EMBL and Gene-Bank), or databases of amino acid sequences deduced from DNA sequences using programs such as BLAST and FASTA, for example, via the Internet.

The polynucleotides of the present invention include isolated polynucleotides. The phrase "isolated polynucleotide" refers to polynucleotides existing in a different form compared to naturally occurring polynucleotides. For example, vectors and polynucleotides integrated in the genome of another organism are included in the isolated polynucleotides. In addition, the isolated polynucleotide includes polynucleotides obtained as a cDNA, PCR product, or restriction fragment. Furthermore, polynucleotides that are used as a portion of a polynucleotide encoding a fusion protein is also encompassed by the phrase "isolated polynucleotide".

The SWISS-PROT database was searched for homology against the amino acid sequence of SEQ ID NO: 2 using the BLAST program. As a result, among known proteins, keto pantoic acid reductase (EC 1.1.1.169) produced by *Salmonella typhimurium* exhibited the highest homology. However, the keto pantoic acid reductase has a different property with the α-keto acid reductase of the present invention and reduces keto pantoic acid in an NADPH-dependent manner.

The score of homology between SEQ ID NO: 2 and this keto pantoic acid reductase was 67/148 (45%) Identity and 95/148 (63%) Positive. Since the homology was calculated based on only a part of the sequence, homology was re-calculated using the Maximum Matching program of Genetyx-win software package (Software Development Co., Ltd.). The newly calculated homology between the two was found to be 46% (J. Biochem., 92, 1173–1177 (1984)). As used herein, the phrase "50% or higher homology" refers to a homology score determined, for example, by the Maximum Matching program.

Furthermore, the present invention relates to proteins comprising the amino acid sequence of SEQ ID NO: 2. The present invention further includes homologs of proteins comprising the amino acid sequence of SEQ ID NO: 2.

As used herein, the phrase a "homolog of the α-keto acid reductase" refers to a protein that comprising the amino acid sequence of SEQ ID NO: 2 in which one or more amino acids have been deleted, substituted, inserted and/or added, and which is functionally equivalent to the protein comprising the amino acid sequence of SEQ ID NO: 2. A homolog of the α-keto acid reductase may contain in the amino acid sequence of SEQ ID NO: 2 mutations of, for example, 100 amino acid residues or less, typically 50 residues or less, preferably 30 residues or less, more preferably 15 residues or less, yet more preferably 10 residues or less, and most preferably 5 amino acid residues or less. In general, to retain the function of a protein, amino acids of the protein are substituted with amino acids that have a similar characteristic to the original amino acid. Such amino acid substitution is called "conservative substitution".

For example, Ala, Val, Leu, Ile, Pro, Met, Phe and Trp are all classified into the group of non-polar amino acids, and have similar properties. Non-charged amino acids include Gly, Ser, Thr, Cys, Tyr, Asn and Gln. Acidic amino acids include Asp and Glu. Basic amino acids include Lys, Arg and His.

As used herein, the phrase "functionally equivalent to the protein comprising the amino acid sequence of SEQ ID NO: 2" means that a protein has the above-described enzymological properties of (i) to (ii). One skilled in the art can obtain polynucleotides encoding a homolog of the α-keto acid reductase by appropriately introducing substitutions, deletions, insertions and/or additions into the DNA of SEQ ID NO: 1 using site-directed mutagenesis (Nucleic Acid Res., 10, 6487 (1982); Methods in Enzymol., 100, 448 (1983); "Molecular Cloning $2^{nd}$ Edition", Cold Spring Harbor Laboratory Press (1989); and "PCR A Practical Approach", IRL Press, 200 (1991)) and so on. A homolog of the α-keto acid reductase of SEQ ID NO: 2 can be obtained by introducing and expressing a polynucleotide encoding the homolog of the α-keto acid reductase into a host.

Furthermore, as used herein, the phrase "homolog of α-keto acid reductase" refers to a protein having a homology of at least 50%, preferably at least 60%, and more preferably 70% or higher to the amino acid sequence of SEQ ID NO: 2. A protein homology search can be carried out against various amino acid sequence databases and DNA databases using programs such as BLAST and FASTA. Available databases include databases of amino acid sequences of proteins, such as SWISS-PROT and PIR; databases of DNA sequences, such as DDBJ, EMBL and Gene-Bank; and databases of amino acid sequences deduced from DNA sequences. All these databases can be used via the Internet.

According to the present invention, an α-keto acid reductase or a homolog thereof may contain additional amino acid sequence, as long as the protein has an functionally equivalent activity to the protein comprising amino acid sequence of SEQ ID NO: 2. For example, a tag sequence such as histidine tag or HA tag can be attached to the protein of the present invention. Alternatively, the protein may be in a form of fusion protein with another protein. Furthermore, the α-keto acid reductase or homolog of the present invention includes fragments of proteins as long as it has a functionally equivalent activity to the protein comprising the amino acid sequence of SEQ ID NO: 2.

A protein having the enzymatic activity of reducing α-keto acid of the present invention can be purified as a substantially pure protein sample. As used herein, the phrase "substantially pure protein sample" refers to a sample that substantially contains no other biomolecules. Specifically, a substantially pure protein sample typically has a purity at dry weight of 75% or higher, or 80% or higher, preferably 85% or higher, more preferably 95% or higher, and yet more preferably 99% or higher. Methods for determining the purity of a protein are known in the art. Specifically, the purity of a protein can be determined using various column chromatographic methods or electrophoretic analysis such as SDS-PAGE.

A polynucleotide encoding the α-keto acid reductase of the present invention can be isolated, for example, by the method described below: designing PCR primers based on the nucleotide sequence of SEQ ID NO: 1, and carrying out PCR using chromosomal DNA or cDNA library from a reductase-producing strain as the template to obtain a DNA of the present invention.

Furthermore, a polynucleotide of the present invention can be prepared using the obtained DNA fragment as a probe by conducting screening of, (a) a library obtained by introducing restriction enzyme fragments of chromosomal DNA derived from a reductase-producing strain into phages or plasmids and transforming *Escherichia coli* cells with the phages or vectors, or (b) a cDNA library, by colony hybridization, plaque hybridization, etc.

Alternatively, a polynucleotide of the present invention can be obtained by analyzing the nucleotide sequence of a DNA fragment obtained by PCR; designing PCR primers based on the analyzed sequence for extending a strand to the outside of the known DNA sequence; digesting the chromosomal DNA of a reductase-producing strain with an appropriate restriction enzyme; and then carrying out reverse-PCR by a self-cyclizing reaction using the DNA as a template (Genetics, 120, 621–623 (1988)). Furthermore, a polynucleotide of the present invention can be obtained by the RACE method (Rapid Amplification of cDNA End, "PCR Jikken Manual (Manual for PCR experiments)", 25–33, HBJ Publishing Bureau).

In addition to the genomic DNAs and cDNAs cloned by the methods as described above, the polynucleotides of the present invention include synthesized DNAs.

The polynucleotides of the present invention can be isolated by above-described methods from a microorganism belonging to the genus selected from the group of:
the genus *Candida*;
the genus *Cryptococcus*;
the genus *Hansenula*;
the genus *Ogataea*;
the genus *Pichia*;
the genus *Rhodosporidium*;
the genus *Rhodotorula*;
the genus *Saccharomyces*;
the genus *Trichosporon*;
the genus *Yamadazyma*;
the genus *Rhodococcus*;
the genus *Amycolatopsis*;
the genus *Alcaligenes*;
the genus *Arthrobacter*;
the genus *Brevibacterium*;
the genus *Comamonas*;
the genus *Corynebacterium*;
the genus *Enterobacter*;
the genus *Enterococcus*;
the genus *Lactobacillus*;
the genus *Leuconostoc*;
the genus *Microbacterium*;
the genus *Micrococcus*;
the genus *Proteus*; and
the genus *Pseudomonas*.

All microorganisms belonging to these genera produce (R)-mandelic acid derivatives using the above-mentioned phenylglyoxylic acid derivative of formula (I) as a substrate.

More specifically, microorganisms belonging to the genera selected from the group listed above include
*Candida ernobii*;
*Candida gropengiesseri*;
*Candida magnoliae*;
*Candida sake*;
*Candida shehatae*;
*Candida sylvatica*;
*Cryptococcus flavus*;
*Cryptococcus humicolus*;
*Cryptococcus marcerans*;
*Hansenula beckii*;
*Hansenula canadensis*;
*Hansenula glucozyma*;
*Ogataea pini*;
*Pichia carsonii*;
*Pichia fabianii*;
*Pichia haplophila*;
*Pichia subpelliculosa*;
*Rhodosporidium dacryoideum*;
*Rhodosporidium diobovatum*;
*Rhodosporidium toruloides*;
*Rhodotorula glutinis*;
*Rhodotorula minuta*;
*Rhodotorula rubra*;
*Saccharomyces cerevisiae*;
*Trichosporon brassicae*;
*Trichosporon pullulans*;
*Yamadazyma castillae*;
*Yamadazyma nakazawae* var. *akitaensis*;
*Yamadazyma scolyti*;
*Rhodococcus erythropolis*;
*Rhodococcus fascians*;
*Rhodococcus obuensis*;
*Rhodococcus rhodochrous*;
*Amycolatopsis orientalis* subsp. *orientalis*;
*Alcaligenes* sp.;
*Arthrobacter protophormiae*;
*Brevibacterium iodinum*;
*Comamonas testosteroni*;
*Corynebacterium ammoniagenes*;
*Enterobacter cloacae*;
*Enterococcus casseliflavus*;
*Enterococcus faecalis*;
*Enterococcus hirae*;
*Lactobacillus viridescens*;

*Lactobacillus mali;*
*Lactobacillus collinoides;*
*Lactobacillus fructivorans;*
*Lactobacillus hilgardii;*
*Leuconostoc mesenteroides* subsp. *dextranicum;*
*Micrococcus luteus;*
*Proteus vulgaris;* and
*Pseudomonas diminuta.*

All the microorganisms can produce (R)-mandelic acid derivatives with a high optical purity.

These microorganisms are available as cell strains from various depositary institutions. Such depositary institutions for cell strains include:
IFO: Institute for Fermentation OSAKA;
DSM: Deutsche Sammlung von Mikroorganismen;
ATCC: American Type Culture Collection;
JCM: Japan Collection of Microorganisms, RIKEN (The Institute of Physical and Chemical Research);
IAM: Institute of Applied Microbiology, University of Tokyo; and
NRIC: NODAI Culture Collection Center, Faculty of Applied
Bio-Science, Tokyo University of Agriculture.

One skilled in the art can also isolate desired microorganisms from various samples.

Vectors expressing the α-keto acid reductase can be prepared by inserting a polynucleotide encoding the α-keto acid reductase of the present invention, which has been isolated by the above-mentioned methods, into known expression vectors.

The α-keto acid reductase of the present invention can also be obtained from a recombinant by culturing a transformant transformed with such expression vectors.

According to the present invention, there is no limitation on the type of microorganism to be transformed to express the α-keto acid reductase, as long as the microorganism can be transformed with a recombinant vector that contains a polynucleotide encoding a polypeptide having the α-keto acid reductase activity and can express the α-keto acid reductase. Available microorganisms include those for which a host-vector system has been developed, for example:
bacteria such as the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus;*
actinomycetes such as the genus *Rhodococcus* and the genus *Streptomyces;*
yeasts such as the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Pichia*, and the genus *Candida;* and
fungi such as the genus *Neurospora*, the genus *Aspergillus*, the genus *Cephalosporium*, and the genus *Trichoderma.*

Procedure for the preparation of a transformant and construction of a recombinant vector suitable for a host can be carried out by employing techniques that are commonly used in the fields of molecular biology, bioengineering, and genetic engineering (for example, see Sambrook et al., "Molecular Cloning", Cold Spring Harbor Laboratories). In order to express, in a microorganism, the gene encoding the α-keto reductase of the present invention whose electron donator is NADH, it is necessary to introduce the DNA into a plasmid vector or phage vector that is stable in the microorganism and let the genetic information being transcribed and translated.

To do so, a promoter, a unit for regulating transcription and translation, is placed upstream of the 5' end of the DNA of the present invention, and preferably a terminator is placed downstream of the 3' end of the DNA. The promoter and the terminator should be functional in the microorganism to be utilized as a host. Available vectors, promoters, and terminators for the above-mentioned various microorganisms are described in detail in "Biseibutugaku Kisokoza 8, Idenshikogaku (Fundamental Course in Microbiology (8): Genetic Engineering)", Kyoritsu Shuppan, specifically for yeasts, in "Adv. Biochem. Eng., 43, 75–102 (1990)" and "Yeast, 8, 423–488 (1992)".

For example, for the genus *Escherichia*, in particular, for *Escherichia coli*, available plasmids include pBR series and pUC series plasmids; available promoters include promoters derived from lac (derived from β-galactosidase gene), trp (derived from the tryptophan operon), tac and trc (which are chimeras of lac and trp), $P_L$ and $P_R$ of λ phage, etc. Available terminators are derived from trpA, phages, rrnB ribosomal RNA, etc. Among various plasmids available for the expression of the reductase of the present invention, vector pSE420D (described in JP-A 2000-189170), commercially available pSE420 (Invitrogen) partly modified at the multi-cloning-site, can be preferably used.

For the genus *Bacillus*, available vectors are pUB110 series and pC194 series plasmids; the vectors can be integrated into host chromosome. Available promoters and terminators are derived from apr (alkaline protease), npr (neutral protease), amy (α-amylase), etc.

For the genus *Pseudomonas*, there are host-vector systems developed for Pseudomonas putida and Pseudomonas cepacia. A broad-host-range vector, pKT240, (containing RSF1010-derived genes required for autonomous replication) based on TOL plasmid, which is involved in decomposition of toluene compounds, is available; a promoter and a terminator derived from the lipase gene (JP-A Hei 5-284973) are available.

For the genus *Brevibacterium*, in particular, for *Brevibacterium lactofennentum*, available plasmid vectors include pAJ43 (Gene, 39, 281 (1985)). Promoters and terminators used for *Escherichia coli* can be utilized without any modification for Brevibacterium.

For the genus *Corynebacterium*, in particular, for *Corynebacterium glutamicum*, plasmid vectors such as pCS11 (JP-A Sho 57-183799) and pCB101 (Mol. Gen. Genet., 196, 175 (1984)) are available.

For the genus *Streptococcus*, plasmid vectors such as pHV1301 (FEMS Microbiol. Lett., 26, 239 (1985)) and pGK1 (Appl. Environ. Microbiol., 50, 94 (1985)) can be used.

For the genus *Lactobacillus*, plasmid vectors such as pAM□1 (J. Bacteriol., 137, 614 (1979)), which were developed for the genus *Streptococcus* can be utilized and promoters that are used for *Escherichia coli* are also usable.

For the genus *Rhodococcus*, plasmid vectors isolated from *Rhodococcus rhodochrous* are available (J. Gen. Microbiol., 138, 1003 (1992)).

For the genus *Streptomyces*, plasmids can be constructed in accordance with the method as described in "Genetic Manipulation of Streptomyces: A Laboratory Manual" (Cold Spring Harbor Laboratories, (1985)) by Hopwood et al. In particular, for *Streptomyces lividans*, pIJ486 (Mol. Gen. Genet., 203, 468–478 (1986)), pKC1064 (Gene, 103, 97–99 (1991)), and pUWL-KS (Gene, 165, 149–150 (1995)) are usable. The same plasmids can also be utilized for *Streptomyces virginiae* (Actinomycetol., 11, 46–53 (1997)).

For the genus *Saccharomyces*, in particular, for *Saccharomyces cerevisiae*, YRp series, YEp series, YCp series, and YIp series plasmids are available; integration vectors (refer EP 537456, etc.), which are integrated into chromosome via homologous recombination with multicopy-ribosomal genes, allow to introduce a gene of interest in multicopy and the gene incorporated is stably maintained in the microorganism; and thus, these types of vectors are highly useful. Available promoters and terminators are derived from genes encoding ADH (alcohol dehydrogenase), GAPDH (glyceraldehyde-3-phosphate dehydrogenase), PHO (acid phosphatase), GAL (β-galactosidase), PGK (phosphoglycerate kinase), ENO (enolase), etc.

For the genus *Kluyveromyces*, in particular, for *Kluyveromyces lactis*, available plasmids are those such as 2-μm plasmids derived from *Saccharomyces cerevisiae*, pKD1 series plasmids (J. Bacteriol., 145, 382–390 (1981)), plasmids derived from pGK11 and involved in the killer activity, KARS (Kluyveromyces autonomous replication sequence) plasmids, and plasmids (see, EP 537456, etc.) capable of being integrated into chromosome via homologous recombination with the ribosomal DNA. Promoters and terminators derived from ADH, PGK, and the like are available.

For the genus *Schizosaccharomyces*, it is possible to use plasmid vectors comprising ARS (autonomous replication sequence) derived from *Schizosaccharomyces pombe* and auxotrophy-complementing selectable markers derived from *Saccharomyces cerevisiae* (Mol. Cell. Biol., 6, 80 (1986)). Promoters such as ADH promoter derived from *Schizosaccharomyces pombe* are usable (EMBO J., 6, 729 (1987)). In particular, pAUR224 is commercially available from TaKaRa Shuzo Co., Ltd.

For the genus *Zygosaccharomyces*, plasmids originating from those such as pSB3 (Nucleic Acids Res., 13, 4267 (1985)) derived from *Zygosaccharomyces rouxii* are available; it is possible to use promoters such as PHO5 promoter derived from *Saccharomyces cerevisiae* and GAP-Zr (Glyceraldehyde-3-phosphate dehydrogenase) promoter (Agri. Biol. Chem., 54, 2521 (1990)) derived from *Zygosaccharomyces rouxii*.

For the genus *Pichia*, a host vector system is developed for *Pichia angusta* (previously called *Hansenula polymorpha*). Although autonomous replication sequences (HARS1 and HARS2) derived from *Pichia angusta* are available as vectors, they are rather unstable. Therefore, multicopy integration to chromosome is effective for microorganisms of the genus *Pichia* (Yeast, 7, 431–443 (1991)). In addition, promoters of AOX (alcohol oxidase) and FDH (formate dehydrogenase) induced by methanol and such are available. Furthermore, host-vector systems originating from autonomous replication sequences (PARS1, PARS2) derived from the genus *Pichia* such as *Pichia pastoris* have been developed (Mol. Cell. Biol., 5, 3376 (1985)), and it is possible to employ a highly efficient promoter such as methanol-inducible AOX promoter, which is available for high-cell-density-culture (Nucleic Acids Res., 15, 3859 (1987)).

For the genus *Candida*, host-vector systems have been developed for *Candida maltosa, Candida albicans, Candida tropicalis, Candida utilis*, etc. An autonomous replication sequence originating from *Candida maltosa* has been cloned (Agri. Biol. Chem., 51, 1587 (1987)), and a vector using the sequence has been developed for *Candida maltosa*. Further, a chromosome-integration vector with a highly efficient promoter unit has been developed for *Candida utilis* (JP-A Hei 08-173170).

For the genus *Aspergillus, Aspergillus niger* and *Aspergillus oryzae* have intensively been studied among fungi, and thus plasmid vectors and chromosome-integration vectors are available, as well as promoters derived from an extracellular protease gene and amylase gene (Trends in Biotechnology, 7, 283–287 (1989)).

For the genus *Trichoderma*, host-vector systems have been developed for *Trichoderma reesei*, and promoters such as that derived from an extracellular cellulase gene are available (Biotechnology, 7, 596–603 (1989)).

There are various host-vector systems developed for plants and animals other than microorganisms. In particular, the systems include those of insect such as silkworm (Nature, 315, 592–594 (1985)), and plants such as rapeseed, maize, potato, etc. These systems are preferably employed to express a large amount of foreign protein.

The present invention relates to a method for producing optically active α-hydroxy acid, which comprises the steps of: (1) reacting an α-keto acid with the α-keto acid reductase of the present invention, a protein having the enzymatic activity of the reductase, a microorganism producing the reductase or the protein, or processed product of the microorganism described above; and (2) collecting the generated optically active α-hydroxy acid. Microorganisms suitably used for producing the α-keto acid reductase or proteins having the enzymatic activity of the reductase in the present invention include all strains of the genus *Leuconostoc*, mutants and variants that have the ability to produce the α-keto acid reductase, as well as transformed strains created by genetic engineering that acquired the ability to produce the enzyme of the present invention. The desired enzymatic reaction can be carried out by contacting a reaction solution containing α-keto acid as a substrate with an enzyme molecule, processed product thereof, culture containing the enzyme molecule, microorganism producing the enzyme, or processed product of the microorganism. However, the procedure for contacting the enzyme with the reaction solution is not restricted to these specific examples.

The processed products of a microorganism having the ability to produce the α-keto acid reductase of the present invention specifically include microorganisms whose cell membrane permeability has been altered by the treatment with a detergent or organic solvent such as toluene; cell-free extracts prepared by fragmenting the cells of microorganisms by a treatment with glass beads or enzymes; and samples partially purified from the cell-free extracts.

Such microorganisms can be cultured based on the knowledge in the field of zymology. Both synthetic and natural culture media can be used so long as the media contains adequate levels of carbon source, nitrogen source, inorganic material, and other nutrients. Both liquid and solid media can be used.

Specifically, taking the assimilation ability of the used microorganism, one or more carbon sources are appropriately selected from the following typical carbon sources:

Saccharides: glucose, fructose, maltose, galactose;
Natural carbohydrates: starch, starch hydrolysate, syrup, blackstrap molasses, wheat, corn, etc.;
Alcohols: glycerol, methanol, ethanol, etc.;
Fatty acids: acetic acid, gluconic acid, pyruvic acid, citric acid, etc.;
Amino acids: glycine, glutamine, asparagine, etc.; and
Carbohydrates: normal paraffin, etc.

Considering the assimilation ability of the used microorganism, one or more nitrogen sources are appropriately selected from the following typical nitrogen sources:

Organic nitrogen compounds:
    meat extract; peptone; yeast extract; soybean hydrolysate; milk casein; casamino acid; various amino acids; corn steep liquor; hydrolysates of other animals, plants and microorganisms; etc.; and
Inorganic nitrogen compounds:
    ammonia; ammonium salt such as ammonium nitrate, ammonium sulfate, and ammonium chloride; nitrate salts such as sodium nitrate; urea; etc.

Inducers can also be used to enhance the α-keto acid reductase producing ability of a microorganism. Such inducers include optically active derivatives of α-hydroxy acid and α-keto acid of interest, and may be used depending on the type of the microorganism to be used.

Furthermore, trace quantities of one or more inorganic salts appropriately selected from magnesium salts, manganese salts, potassium salts, calcium salts, sodium salts, copper salts, zinc salts, and such of phosphate, hydrochloride, nitrate, acetate, etc. may be used for the culture. Moreover, according to the need, antifoaming agents such as vegetable oils, detergents and silicon may be added to the liquid medium.

Microorganisms can be cultured in a liquid medium containing the above-described components of medium by typical culture methods such as shaking culture, aerated spinner culture, continuous culture, and fed-batch culture.

Culture conditions can be appropriately selected depending on the types of microorganism, culture, and culture method. There is no limitation on the type of culture conditions as long as the strain proliferates and the proliferated cells have the ability to convert phenylglyoxylic acid derivative into mandelic acid derivative.

According to the present invention, the microorganisms are typically cultured under a temperature condition of 15 to 70° C., preferably 25 to 40° C., adjusting the pH at the start of culture to pH 4 to 10, preferably to pH 6 to 8. There is no limitation on the duration of culture as long as cells of the microorganisms that have the ability to convert phenylglyoxylic acid derivative to mandelic acid derivative can be obtained. Typically, the culture is continued for 1 to 7 days, preferably 1 to 3 days.

Processed products of such cells of microorganisms of the present invention include, for example, freeze-dried cells, acetone-dried cells, autolysates of cells, cell extracts, crushed cells, and sonicated cells of the above-mentioned microorganism. The processed products further include enzymes purified from cell extracts by the combined use of known methods, and may be purified enzymes or partially purified enzymes.

Furthermore, before use, the cells of microorganisms of the present invention or processed products thereof can be immobilized, for example, by known methods, such as the polyacrylamide method, the sulfur-containing polysaccharide gel method (κ-carrageenan gel method, etc.), the alginate-gel method, the agar-gel method, or the ion-exchange resin method.

A method for asymmetric reduction using an enzyme or a microorganism of the present invention can be conducted by culturing a microorganism under the above-mentioned appropriate conditions which ensure the induction of the enzyme, and adding a reaction substrate to the obtained liquid medium, cells harvested from the liquid medium, or processed product of the cells. Alternatively, the asymmetric reduction can be conducted in parallel with the culture of the microorganism for 1 to 7 days under the same culture conditions, i.e., pH and temperature range as described above.

An exemplary reaction condition is as follows:
pH: 4.0 to 9.0, preferably 5.0 to 8.0;
temperature: 15 to 50° C., preferably 25 to 40° C.; and
reaction time: 4 hours to 7 days.

In general, a better result can be expected by separately carrying out the asymmetric reduction than together with the culture of microorganisms.

When the asymmetric reduction is conducted parallel with the culture of microorganisms, an efficient reaction can be expected by conducting the reaction in the presence of saccharide, alcohol or sugar alcohol as an energy source for the reduction. Such saccharides include glucose, fructose, and sucrose; such alcohols include ethanol, isopropanol, and glycerol; and such sugar alcohols include sorbitol. The amount of a compound to be added as the energy source for the reduction depends on the amount of the reaction substrate, i.e., α-keto acid.

When the pH of the reaction solution changes in accordance with the consumption of the reduction energy source, an improved reactivity can be maintained by adjusting the pH within a certain range using an appropriate acid or alkali.

When viable cells of microorganisms are used in the present invention, a detergent is preferably added in the reaction to reduce the reaction time. There is no limitation on the type of detergent to be used for this purpose as long as the detergent increases the cell-membrane permeability of the viable cells of microorganism. Such detergents include cetylpyridinium bromide, cetyl-trimethylammonium bromide, Triton X-100, para-isooctylphenyl ether, Tween 80, and Span 60, and are preferably used at a concentration of approximately 0.0001% to 1% in a reaction solution.

A similar effect can be achieved by adding an organic solvent to the reaction solution. There is no limitation on the type of organic solvent to be used for this purpose, as long as it increases the cell-membrane permeability of the viable cells of microorganism. Such organic solvents include toluene and xylene, and are preferably used at a concentration of approximately 0.0001% to 1% in the reaction solution.

Instead of adding a detergent or organic solvent to the reaction solution, cells of microorganisms with increased membrane permeability can be obtained by treating the harvested cells with the detergent or organic solvent.

The amount of typical by-product generated by the asymmetric reduction of the present invention may be sometimes increased under an aerobic condition. In such cases, a high yield of the object product can be expected by performing the reaction under an anaerobic or limited oxygen condition. Specifically, for example, an increase in yield can be expected by conducting the reaction while passing nitrogen gas through the reaction solution or filling the gaseous phase with nitrogen gas.

α-keto acids used as substrate in the method for producing optically active α-hydroxy acids according to the present invention includes, for example, the phenylglyoxylic acid derivative of formula (I) shown below:

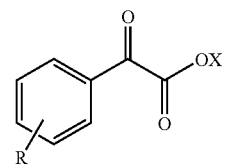

Formula (I)

wherein X is hydrogen atom, alkaline metal or alkaline earth metal; and R indicates one or more substituents at the ortho, meta or para position selected from the group of halogen atom, hydroxyl group, $C_{1-3}$ alkyl group, $C_{1-3}$ alkoxy group, $C_{1-3}$ thioalkyl group, amino group, nitro group, mercapto group, phenyl group and phenoxy group.

Specific examples of the substituent include: halogen atoms such as bromine atom, chlorine atom, fluorine atom and iodine atom; branched or non-branched lower alkyl groups having 1 to 3 carbon atoms; alkoxy groups such as methoxy group and ethoxy group; thioalkyl groups such as thiomethyl group; amino groups; nitro groups; mercapto groups; phenyl groups; phenoxy groups, etc. The compound may contain one or more of such substituents, and may further form a ring structure like lower alkylenedioxy groups such as methylenedioxy, ethylenedioxy and trimethylenedioxy groups.

When the compound of formula (I) is a metal salt (i.e., x is metal atom), the metal atom may be monovalent metals such as sodium and potassium, or divalent metals such as calcium and magnesium.

According to the present invention, for example, 2-halophenyl glyoxylic acid compounds such as 2-chlorophenyl glyoxylic acid (R at the ortho position is Cl) and 2-bromophenyl glyoxylic acid may be used as the compound of formula (I) (i.e., substrate).

Alternatively, 3-halophenyl glyoxylic acid compounds such as 3-chlorophenyl glyoxylic acid (R at the meta position is Cl) and 3-bromophenyl glyoxylic acid may be used as the substrate in the present invention.

Furthermore, the halogen of the above-described compounds may be substituted with hydroxyl group (R is OH) or alkyl group (R is methyl or ethyl) in the present invention.

These substrate compounds can be produced by conventional methods. For example, 2-chlorophenyl glyoxylic acid shown in the Examples can be synthesized via 2-chlorophenyl-oxo-acetonitrile from 2-chlorobenzoyl chloride as the starting material (Bull. Soc. Chim. Fr., 850, 851 (1959)).

Specific examples of α-keto acids that can be used in the method for producing optically active α-hydroxy acids of the present invention and corresponding α-hydroxy acid products include:

phenylglyoxylic acid: (R)-mandelic acid;
2-ketoisovaleric acid:(R)-2-hydroxyisovaleric acid;
2-ketoisocaproic acid: (R)-2-hydroxyisocaproic acid;
3-chlorophenyl glyoxylic acid: (R)-3-chloromandelic acid;
keto pantoic acid: (R)-pantoic acid;
trimethylpyruvic acid: (R)-2-hydroxy-3,3-dimethylbutylate; and
2-chlorophenyl glyoxylic acid: (R)-2-chloromandelic acid.

The reaction substrate of the present invention, i.e., α-keto acid can be used at an adequate concentration which ensures efficient generation of the product of interest. Since the solubility of α-keto acid in aqueous solvent is high, it can be used at a high concentration within a range that does not inhibit the reaction. An exemplary concentration range of α-keto acid in the reaction solution is 0.1 to 50% w/v, and preferably 1 to 20% w/v. The α-keto acid may be added by any method, e.g., addition at once (batch operation), stepwise addition (fed-batch operation), or continuous addition (feed operation).

As used herein, the phrase "optically active α-hydroxy acid" refers to α-hydroxy acid wherein one of the optical isomers is more abundant than the other. According to the present invention, a preferred optically active α-hydroxy acid has typically an enatiomeric excess of 50% ee (enantiomeric excess) or higher, preferably 80% ee or higher, more preferably 90% ee or higher, and yet more preferably 95% ee or higher. The enantiomeric excess of an optically active α-hydroxy acid can be determined, for example, using an optical resolution column or such. Generally, an "optical isomer" of the present invention may also be called "optically active substance" or "enantiomer".

Regeneration of NADH from $NAD^+$, which is generated from NADH in association with the above-mentioned reduction reaction, can be achieved by utilizing the $NAD^+$-reducing abilities of microorganisms (glycolysis, C1 compound assimilatory pathway of methylotroph, etc.). Such $NAD^+$-reducing ability can be potentiated by adding glucose, ethanol, formic acid, etc. to the reaction system. Alternatively, NADH can also be regenerated by adding a microorganism, processed product thereof, or an enzyme having the ability to convert $NAD^+$ to NADH to the reaction system. For example, NADH regeneration can be achieved using microorganisms containing glucose dehydrogenase, formate dehydrogenase, alcohol dehydrogenase, amino acid dehydrogenase, or organic acid dehydrogenase (malate dehydrogenase, etc.); processed products thereof; and partially purified or purified enzymes. These components required for the NADH regeneration reaction can be added directly or after being immobilized on a support to the reaction system to produce α-hydroxy acid of the present invention. Alternatively, the components may be contacted via a NADH permeable membrane with the reaction system to produce α-hydroxy acid of the present invention.

When a viable cell of a microorganism transformed with a recombinant vector comprising a DNA of the present invention is used in the above-described method for producing α-hydroxy acid, in some cases, additional reaction system for NADH regeneration can be omitted. Specifically, the use of a microorganism with a high NADH regenerating activity as the transformant for the reduction reaction allows efficient reduction reaction without any addition of enzymes for regenerating NADH. Alternatively, a gene encoding glucose dehydrogenase, formate dehydrogenase, alcohol dehydrogenase, amino acid dehydrogenase, or organic acid dehydrogenase (malate dehydrogenase, etc.) that can be used to regenerate NADH may be introduced into a host simultaneously with a DNA encoding NADH-dependent α-keto acid reductase of the present invention to express the NADH regeneration enzyme and the NADH-dependent α-keto acid reductase, and finally achieve a reduction reaction with a higher efficiency. Methods to introduce two or more of these genes into a host include: (1) transformation of the host with two or more recombinant vectors separately inserted with respective genes and which vectors have different replication origins to each other to avoid incompatibility; (2) introduction of a single vector inserted with both (or all) genes; and (3) introduction of both (or all) or one (or more) of the genes into the chromosome of the host.

In case of inserting multiple genes into a single vector, regulatory regions for expression, such as promoter and terminator may be ligated to each of the genes, or the genes may be expressed as a polycistronic operon such as lactose operon.

Available NADH-regenerating enzymes are exemplified by formate dehydrogenase derived from *Mycobacterium vaccae* and glucose dehydrogenase derived from *Bacillus subtilis*. Specifically, recombinant vectors pSF-LMK1 (comprising genes encoding an α-keto acid reductase and a formate dehydrogenase) and pSG-LMK1 (comprising genes encoding an α-keto acid reductase and a glucose dehydrogenase) are preferably used in the method of the present invention.

The reduction reaction using the enzyme of the present invention can be performed in water; organic solvent immiscible with water, for example, ethyl acetate, butyl acetate, toluene, chloroform, or n-hexane; two-phase system of the water immiscible organic solvent and an aqueous solvent; or mixed solvent system of an organic solvent that is miscible with water, for example, methanol, ethanol, isopropylalcohol, acetonitrile, acetone, or dimethylsulfoxide. The reaction of the present invention can be conducted using immobilized enzyme, membrane reactor, etc.

The reaction of the present invention can be conducted at a reaction temperature of 4° C. to 60° C., preferably 15° C. to 37° C.; at pH 3 to 11, preferably pH 5 to −9; and at a substrate concentration of 0.01% to 50%, preferably 0.1% to 20%, and more preferably 0.1% to 10%. If required, coenzyme $NAD^+$ or NADH can be added to the reaction system at a concentration of 0.001 mM to 100 mM, preferably 0.01 mM to 10 mM. The substrate may be added at once at the start of the reaction. However, continuous or stepwise addition of the substrate is preferable in order to prevent the substrate concentration from becoming too high.

When a glucose dehydrogenase is used for regenerating NADH, glucose is added to the reaction system. Similarly, formic acid and ethanol or isopropanol are added when formate dehydrogenase and alcohol dehydrogenase are used, respectively. These compounds may be added, in molar ratio, 0.1 to 20-fold excess, and preferably 1 to 5-fold excess over the substrate α-keto acid. On the other hand, the NADH-regenerating enzyme such as glucose dehydrogenase, formate dehydrogenase, or alcohol dehydrogenase can be added, in terms of enzyme activity, 0.1 to 100-fold excess, and preferably about 0.5 to 20-fold excess over the NADH-dependent α-keto acid reductase of the present invention.

Thus, a phenylglyoxylic acid derivative is asymmetrically reduced by the reaction of the present invention to produce an optically active mandelic acid derivative. The resulting optically active mandelic acid derivative can readily be isolated according to conventional methods. For example, an optically active mandelic acid derivative can be collected as crystal by the following procedure: (1) removing insoluble materials such as cells from the reaction solution by centrifugation; (2) lowering the pH of the reaction solution preferably to about pH 1 with an appropriate mineral acid, for example, sulfuric acid or hydrochloric acid; and (3) following extraction with ethyl acetate, butyl acetate, toluene, hexane, benzene, methyl isobutyl ketone, methyl tert-butyl ester, diethyl ether, or the like, the solution is concentrated under reduced pressure.

Furthermore, in order to improve the purity of the reaction product, the concentrated reaction product is dissolved in a small volume of acetone, and purified by silica gel column chromatography using hexane-acetone mixed solvent as the elution solution to give a highly purified sample. Alternatively, the reaction product can be easily separated from impurities by dissolving the reaction product in benzene, toluene or hexane-ethyl acetate mixed solvent while being heated, and cooling the solution for recrystallization.

Optically active α-hydroxy acid can be efficiently produced by the asymmetric reduction reaction using a microorganism of the present invention. A high-yield can be expected by the method of the present invention. Thus the method of the present invention is advantageous for industrial application. Optically active α-hydroxy acids produced according to the present invention include optically active mandelic acid derivatives which are useful as optical resolution agents, and as raw materials for the synthesis of optically active pharmaceuticals and pesticides. More specifically, optically active mandelic acid derivatives are used as intermediates in the synthesis of anti-platelet agents or anti-obesity drugs, and in preferential crystallization.

The present invention provides an NADH-dependent α-keto acid reductase which is useful for the production of optically active α-hydroxy acids. The present invention also provides a method for efficiently producing (R)-2-chloromandelic acids with high optical purity from 2-chlorophenyl glyoxylic acid using the enzyme.

The present invention is illustrated in more detail below with reference to Examples, but is not to be construed as being limited thereto. Any patents, patent applications, and publication cited herein are incorporated by reference.

The abbreviations in the column of strain name in the table refer to the following depositary institutions:

IFO: Institute for Fermentation, OSAKA;

DSM: Deutsche Sammlung von Mikroorganismen;

ATCC: American Type Culture Collection;

JCM: Japan Collection of Microorganisms, RIKEN (The Institute of Physical and Chemical Research);

IAM: Institute of Applied Microbiology, University of Tokyo; and

NRIC: NODAI Culture Collection Center, Faculty of Applied Bio-Science, Tokyo University of Agriculture.

Equivalents

The contents of all references, pending patent applications and published patent applications, cited throughout this application, including those referenced in the background section, are hereby incorporated by reference.

EXAMPLE 1

Synthesis of Substrate 2-chlorophenyl Glyoxylic Acid 17.5 g (0.1 mol) 2-chlorobenzoyl chloride, 11.65 g (0.13 mol) copper (I) cyanide, and 8 mL of acetonitrile in 15 mL of toluene was refluxed for 3 hours, and then cooled to room temperature. Insoluble material was filtered and the residue was washed with toluene. The solvent in the resulting filtrate was evaporated under reduced pressure, and the residue was distilled to yield 12.3 g of 2-chlorophenyloxoacetonitrile (yield=75%).

16.5 g (0.1 mol) of the prepared 2-chlorophenyloxoacetonitrile was incubated in 110 mL of concentrated hydrochloric acid at room temperature for 5 days, and 1100 mL of water was added thereto. The resulting mixture was extracted with ether, and the solvent of the ether layer was removed under reduced pressure. The residue was recrystallized in tetrachloromethane to yield white crystal (16.6 g).

The compound (yield=90%) was confirmed to be 2-chlorophenyl glyoxylic acid of formula (III) by spectral analyses of $^1$H-NMR, MS and IR.

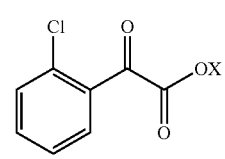

Formula (III)

EXAMPLE 2

Screening of Yeast

Liquid medium (pH 6.0) containing 3 g/L yeast extract, 3 g/L malt extract, 20 g/L glucose, and 5 g/L polypeptone was aliquoted into test tubes (18-mm diameter)(4 mL to each tube), and then was sterilized by heating in autoclave at 121° C. for 15 minutes. Each of the strains of microorganisms listed below in Table 1 was inoculated to respective tubes using a platinum loop, and then was cultured with shaking at 30° C. for 48 hours.

Following centrifugation of 2 mL of the obtained culture media, 1 mL of 100 mM phosphate buffer (pH 7.0) containing 10 mg 2-chlorophenyl glyoxylic acid and 10 mg glucose was added to the cells of microorganism collected by the centrifugation. The cells were reacted with shaking at 30° C. for 48 hours.

The cells were removed from the reaction solution by centrifugation, and 2-chloromandelic acid in the supernatant was quantified by liquid chromatography using a C18 reverse-phase column (Wakosil II 5C18 HG 4.6 mm×250 mm; Wako Pure Chemical Industries Ltd.). The column temperature was set to 40° C. The compound of interest was eluted with 50 mM phosphate buffer (pH 2.5): acetonitrile=3:1 with a flow rate of 1 mL/min, and the UV absorbance at 254 nm was measured for quantification.

Furthermore, 2-chloromandelic acid was extracted with ethyl acetate from the reaction solution to remove the solvent, and the optical purity of the extracted 2-chloromandelic acid was determined by liquid chromatography using an optical resolution column. Chiralcell OJ-H (CHIRALCEL OJ-H 4.6 mm×150 mm; Daicel Chemical Industries, Ltd.) was used as the optical resolution column. The compound of interest was eluted with n-hexane:isopropanol:trifluoroacetic acid=85:15:0.1 at a flow rate of 1.5 mL/min, and the UV absorbance at 254 nm was detected to measure the optical purity.

The analysis result is shown in Table 1. The production of the optically active (R)-2-chloromandelic acid was confirmed.

TABLE 1

| Strain name | Accumulation amount (g/L) | Optical activity (%) |
|---|---|---|
| Candida sake IFO 1517 | 0.661 | 100 |
| Candida shehatae IFO 1983 | 0.690 | 100 |
| Candida silvatica IFO 10311 | 1.27 | 99.8 |
| Candida magnoliae DSM 70638 | 0.784 | 92.0 |
| Candida ernobii DSM 70858 | 0.508 | 84.1 |
| Cryptococcus marcerans IFO 1870 | 3.68 | 100 |
| Cryptococcus flavus IFO 0407 | 3.06 | 100 |
| Cryptococcus humicolus IFO 0760 | 1.20 | 99.4 |
| Hansenula glucozyma DSM 70271 | 0.232 | 99.3 |
| Hansenula canadensis DSM 70281 | 0.271 | 99.1 |
| Hansenula beckii DSM 70266 | 0.268 | 87.3 |
| Ogataea pini IFO 1342 | 0.654 | 100 |
| Pichia fabianii IFO 1253 | 0.242 | 98.4 |
| Pichia carsonii DSM 70392 | 0.675 | 97.5 |
| Pichia subpelliculosa IFO 0808 | 0.342 | 94.9 |
| Pichia haplophila DSM 70365 | 0.299 | 94.7 |
| Rhodosporidium toruloides IFO 1535 | 1.41 | 100 |
| Rhodosporidium diobovatum IFO 1830 | 1.16 | 100 |
| Rhodosporidium toruloides IFO 0559 | 2.92 | 96.2 |
| Rhodotorula rubra IFO 0383 | 0.635 | 100 |
| Rhodotorula glutinis IFO 0898 | 0.511 | 100 |
| Saccharomyces cerevisiae IFO 0203 | 0.166 | 94.0 |
| Trichosporon brassicae IFO 1584 | 1.49 | 100 |
| Trichosporon pullulans IFO 1232 | 0.339 | 100 |
| Yamadazyma castillae IFO 1823 | 1.21 | 100 |
| Yamadazyma scolyti IFO 1280 | 0.511 | 100 |
| Yamadazyma nakazawae var. akitaensis IFO 1669 | 0.454 | 96.0 |

EXAMPLE 3

Screening of Bacteria and Actinomycetes

Bouillon medium (Nissui Pharmaceutical Co., Ltd.) was aliquoted (4 mL) into test tubes (18-mm diameter), and was heat sterilized in autoclave at 121° C. for 15 minutes. Each of the strains of microorganisms listed below in Table 2 was inoculated to respective tubes using a platinum loop, and was cultured with shaking at 30° C. for 48 hours.

Cells of microorganism were collected by centrifugation of 2 mL of the obtained liquid culture medium, and 1 mL of 100 mM phosphate buffer (pH 7.0) containing 10 mg 2-chlorophenyl glyoxylic acid and 10 mg glucose was added thereto. The cells were reacted with shaking at 30° C. for 48 hours.

The cells of microorganism were removed from the reaction solution by centrifugation. 2-chloromandelic acid in the obtained supernatant was quantified and its optical purity was determined according to the procedures described in Example 2.

The analysis result is shown in Table 2. The production of optically active (R)-2-chloromandelic acid was confirmed.

TABLE 2

| Strain name | Accumulation amount (g/L) | Optical activity (%) |
|---|---|---|
| Amycolatopsis orientalis subsp. orientalis IFO 12806 | 2.42 | 97.9 |
| Rhodococcus erythropolis JCM 6822 | 2.28 | 100 |
| Rhodococcus fascians IFO 12077 | 4.79 | 99.7 |
| Rhodococcus obuensis JCM 6048 | 2.72 | 99.4 |
| Rhodococcus rhodochrous DSM 363 | 1.42 | 100 |
| Alcaligenes sp. IAM 1015 | 1.47 | 97.8 |
| Arthrobacter protophormiae IFO 12128 | 5.31 | 98.7 |
| Brevibacterium iodinum IFO 3558 | 2.29 | 93.4 |
| Comamonas testosteroni IFO 12048 | 2.45 | 95.4 |
| Corynebacterium ammoniagenes IFO 12072 | 6.92 | 98.2 |
| Enterobacter cloacae IFO 3320 | 3.06 | 98.7 |
| Micrococcus luteus IFO 3333 | 2.00 | 100 |
| Proteus vulgaris IFO 3851 | 2.49 | 100 |
| Pseudomonas diminuta IFO 12697 | 2.76 | 98.7 |

EXAMPLE 4

Screening of Lactic Acid Bacteria

MRS medium (Lactobacilli MRS broth; Difco Laboratories) was aliquoted (4 mL) into test tubes (18-mm diameter), and was heat sterilized in autoclave at 121° C. for 15 minutes. Each of the strains of microorganisms listed below in Table 3 was inoculated to respective tubes using a platinum loop, and then was cultured with shaking at 30° C. for 48 hours.

Cells of microorganism were collected by centrifugation of 2 mL of the obtained liquid culture medium, and 1 mL of 100 mM phosphate buffer (pH 7.0) containing 10 mg 2-chlorophenyl glyoxylic acid and 10 mg glucose was added thereto. The cells were reacted with shaking at 30° C. for 48 hours.

The cells of microorganisms were removed from the reaction solution by centrifugation. 2-chloromandelic acid in the obtained supernatant was quantified and its optical purity was determined according to the procedures described in Example 2.

The analysis result is shown in Table 3. The production of optically active (R)-2-chloromandelic acid was confirmed.

TABLE 3

| Strain name | Accumulation amount (g/L) | Optical activity (%) |
|---|---|---|
| *Enterococcus casseliflavus* NRIC 0106 | 3.63 | 99.0 |
| *Enterococcus faecalis* IFO 12966 | 3.89 | 99.0 |
| *Enterococcus hirae* ATCC 49611 | 1.15 | 98.4 |
| *Lactobacillus viridescens* NRIC 1073 | 3.09 | 99.1 |
| *Lactobacillus mali* NRIC 1076 | 2.02 | 99.1 |
| *Lactobacillus collinoides* NRIC 1049 | 5.37 | 99.0 |
| *Lactobacillus fructivorans* NRIC 0224 | 5.22 | 98.9 |
| *Lactobacillus hilgardii* DSM 20051 | 8.06 | 98.8 |
| *Leuconostoc mesenteroides* subsp. *dextranicum* NRIC 1085 | 9.49 | 99.1 |
| *Leuconostoc mesenteroides* subsp. *dextranicum* ATCC 17072 | 8.87 | 99.8 |

EXAMPLE 5

Screening for Lactic Acid Bacteria Producing (S)-Isomer

MRS medium (Lactobacilli MRS broth; Difco Laboratories) was aliquoted (4 mL) into test tubes (18-mm diameter), and was heat sterilized in autoclave at 121° C. for 15 minutes. Each of the strains of microorganisms listed below in Table 4 was inoculated to respective tubes using a platinum loop, and then was cultured with shaking at 30° C. for 48 hours.

Cells of microorganism were collected by centrifugation of 2 mL of the obtained liquid culture medium, and 1 mL of 100 mM phosphate buffer (pH 7.0) containing 10 mg 2-chlorophenyl glyoxylic acid and 10 mg glucose was added thereto. The cells were reacted with shaking at 30° C. for 48 hours.

The cells of microorganisms were removed from the reaction solution by centrifugation. 2-chloromandelic acid in the obtained supernatant was quantified and its optical purity was determined according to the procedures described in Example 2.

The result of the analysis is shown in Table 4. The production of optically active (R)-2-chloromandelic acid was confirmed.

TABLE 4

| Strain name | Accumulation amount (g/L) | Optical activity (%) |
|---|---|---|
| *Lactobacillus halotolerans* NRIC 1627 | 1.32 | −100 |
| *Leuconostoc mesenteroides* subsp. *cremoris* IAM 1087 | 2.07 | −17.6 |

Comparative Example

Liquid medium (pH 6.0) containing 3 g/L yeast extract, 3 g/L malt extract, 20 g/L glucose and 5 g/L polypeptone was aliquoted (4 mL) into test tubes (18-mm diameter), and were heat sterilized in autoclave at 121° C. for 15 minutes. *Candida famata* strain IFO 0856 described in Japanese Patent No. 03146641 (JP-A Hei 6-7179) was inoculated to the tubes using a platinum loop, and was cultured with shaking at 30° C. for 48 hours.

Cells of microorganism were collected by centrifugation of 2 mL of the obtained liquid culture medium and 1 mL of 100 mM phosphate buffer (pH 7.0) containing 10 mg 2-chlorophenyl glyoxylic acid and 10 mg glucose was added thereto. The cells were reacted with shaking at 30° C. for 48 hours.

The cells of microorganism were removed from the reaction solution by centrifugation. 2-chloromandelic acid in the obtained supernatant was quantified according to the procedure described in Example 2.

2-Chloromandelic acid could not be detected in the supernatant.

EXAMPLE 6

Synthesis of Substrate 3-chlorophenyl Glyoxylic Acid 43.8 g (0.1 mol) 3-chlorobenzoyl chloride, 29.1 g (0.13 mol) copper (I) cyanide, and 20 mL acetonitrile in 37 mL toluene was refluxed for 3 hours, and then cooled to room temperature. Insoluble material was filtered and the residue was washed with toluene. The solvent in the resulting filtrate was evaporated under reduced pressure, and the residue was distilled to yield 28 g 3-chlorophenyloxoacetonitrile (yield=68%).

15 g (0.1 mol) of the prepared 3-chlorophenyloxoacetonitrile was reacted in 110 mL of concentrated hydrochloric acid at room temperature for 5 days, 1100 mL of water was added thereto, extracted with ether, and the solvent in the ether layer was evaporated under reduced pressure. The residue was recrystallized in tetrachloromethane to yield white crystal (15.1 g).

The compound (yield=90%) was confirmed to be 3-chlorophenyl glyoxylic acid of formula (III) by spectral analyses of $^1$H-NMR, MS and IR.

EXAMPLE 7

Screening of Bacteria (2)

Bouillon medium (Nissui Pharmaceutical Co., Ltd.) was aliquoted (4 mL) into test tubes (18-mm diameter), and was heat sterilized in autoclave at 121° C. for 15 minutes. Each of the strains of microorganisms listed below in Table 5 was inoculated to respective tubes using a platinum loop, and was cultured with shaking at 30° C. for 48 hours.

Cells of microorganism were collected by centrifugation of 2 mL of the obtained liquid culture medium, and 1 mL of 100 mM phosphate buffer (pH 7.0) containing 10 mg 3-chlorophenyl glyoxylic acid and 10 mg glucose was added thereto. The cells were reacted with shaking at 30° C. for 48 hours.

The cells of microorganisms were removed from the reaction solution by centrifugation. 3-chloromandelic acid in the obtained supernatant was quantified by liquid chromatography using a C18 reverse-phase column (Wakosil II 5C18 HG 4.6 mm×250 mm; Wako Pure Chemical Industries). 50 mM phosphate buffer (pH 2.5): acetonitrile=3:1 was used as the elution solvent. The elution was conducted at a flow rate of 1 mL/min, and quantification was performed by detecting the UV absorbance at 254 nm.

Furthermore, 3-chloromandelic acid was extracted with ethyl acetate from the reaction solution, the solvent was removed, and then the optical purity of 3-chloromandelic acid was determined by liquid chromatography using an optical resolution column, Chiralcell OJ-H (CHIRALCEL OJ-H 4.6 mm×150 mm; Daicel Chemical Industries, Ltd.). Elution solution n-hexane:isopropanol:trifluoroacetic acid=85:15:0.1 was passed through the column at a flow rate of 1.5 mL/min, and the UV absorbance at 254 nm was detected for the measurement of the optical purity.

The analysis result is shown in Table 5. The production of optically active (R)-3-chloromandelic acid was confirmed.

TABLE 5

| Strain name | Accumulation amount (g/L) | Optical activity (%) |
|---|---|---|
| Enterobacter cloacae IFO 3320 | 1.09 | 99.0 |
| Arthrobacter protophormiae IFO 12128 | 3.06 | 98.8 |

EXAMPLE 8

Screening of Lactic Bacteria (2)

MRS medium (Lactobacilli MRS broth; Difco Laboratories) was aliquoted (4 mL) into test tubes (18-mm diameter), and was heat sterilized in autoclave at 121° C. for 15 minutes. Each of the strains of microorganisms listed below in Table 5 was inoculated to respective tubes using a platinum loop, and was cultured with shaking at 30° C. for 48 hours.

Cells of microorganism were collected by centrifugation of 2 mL of the obtained liquid culture medium, and 1 mL of 100 mM phosphate buffer (pH 7.0) containing 10 mg 3-chlorophenyl glyoxylic acid and 10 mg glucose was added thereto. The cells were reacted with shaking at 30° C. for 48 hours.

The cells of microorganisms were removed from the reaction solution by centrifugation. 3-chloromandelic acid in the obtained supernatant was quantified and its optical purity was determined according to the procedures described in Example 7.

The analysis result is shown in Table 6. The production of optically active (R)-3-chloromandelic acid was confirmed.

TABLE 6

| Strain name | Accumulation amount (g/L) | Optical activity (%) |
|---|---|---|
| Enterococcus faecalis IFO 12966 | 6.90 | 99.0 |
| Enterococcus casseliflavus NRIC 0106 | 5.44 | 98.8 |
| Lactobacillus collinoides NRIC 1049 | 0.323 | 98.5 |
| Lactobacillus viridescens NRIC 1073 | 3.00 | 99.1 |
| Leuconostoc mesenteroides subsp. dextranicum NRIC 1085 | 3.11 | 99.0 |
| Leuconostoc mesenteroides subsp. dextranicum ATCC 17072 | 4.72 | 99.0 |
| Lactobacillus hilgardii DSM 20051 | 0.706 | 99.1 |
| Lactobacillus fructivorans NRIC 0224 | 0.156 | 98.9 |

EXAMPLE 9

Purification of α-keto Acid Reductase

Leuconostoc mesenteroides subsp. dextranicum strain (ATCC 17072) was cultured in 1.2 L of MRS medium (Lactobacilli MRS broth, Difco Laboratories), and then cells were harvested by centrifugation. The resulting wet cells were suspended in 50 mM Tris-HCl buffer (pH 8.5) containing 0.02% 2-mercaptoethanol and 2 mM phenylmethanesulfonyl fluoride (PMSF), and crushed with a bead beater (Biospec Products, Inc.). Then, cell debris was removed by centrifugation to prepare cell-free extract. Protamine sulfate was added to the cell-free extract and the mixture was centrifuged to prepare supernatant avoid of nucleic acid. Ammonium sulfate was added to the supernatant at a final concentration of 30%. The mixture was loaded onto phenyl-Sepharose HP (2.6 cm×10 cm) equilibrated with standard buffer (10 mM Tris-HCl buffer (pH 8.5), 0.01% 2-mercaptoethanol, 10% glycerol) containing 30% ammonium sulfate, and eluted with a 30% to 0% concentration gradient of ammonium sulfate. NADH-dependent 2-chlorophenyl glyoxylic acid-reducing activity was detected in fractions eluted with the gradient. The peak fractions eluted were collected and concentrated by ultrafiltration.

The concentrated enzyme solution was dialyzed against the standard buffer. The solution was loaded onto a Mono Q (0.5 cm×5 cm) column equilibrated with the same buffer, followed by elution with a 0 M to 0.5 M concentration gradient of sodium chloride. The active fractions eluted were collected and concentrated enzyme solution was prepared by ultrafiltration.

The concentrated enzyme solution was dialyzed against 5 mM potassium phosphate buffer (pH 8.0) containing 0.01% 2-mercaptoethanol and 10% glycerol. Then the solution was loaded onto a hydroxyapatite column (0.5 cm×10 cm) equilibrated with the same buffer, followed by elution with a 5 mM to 350 mM concentration gradient of potassium phosphate buffer (pH 8.0). A fraction exhibiting the highest specific activity among the eluted active fractions was analyzed by SDS-PAGE to detect a single band (FIG. 1).

Specific activity of the purified enzyme was 3,810 U/mg. The outline of purification is shown in Table 7.

TABLE 7

Outline of purification

| Purification step | Protein (mg) | Enzyme activity (U) | Relative activity (U/mg) |
|---|---|---|---|
| Cell-free extract | 1,950 | 5,330 | 2.7 |
| Supernatant without nucleic acid | 973 | 4,290 | 4.4 |
| Solution purified by Phenyl-Sepharose column | 63.0 | 4,125 | 65.7 |
| Solution purified by Mono Q column | 7.22 | 2,046 | 284 |
| Solution purified by hydroxyapatite column | 0.108 | 412 | 3810 |

EXAMPLE 10

Determination of Molecular Weight of α-keto Acid Reductase

The molecular weight of the subunit of the enzyme obtained in Example 9 was determined to be approximately 35,000 daltons by SDS-PAGE. On the other hand, the molecular weight determined using a Superdex G200 gel filtration column was approximately 63,000 daltons.

EXAMPLE 11

Optimum pH of α-keto Acid Reductase.

Figure 2:
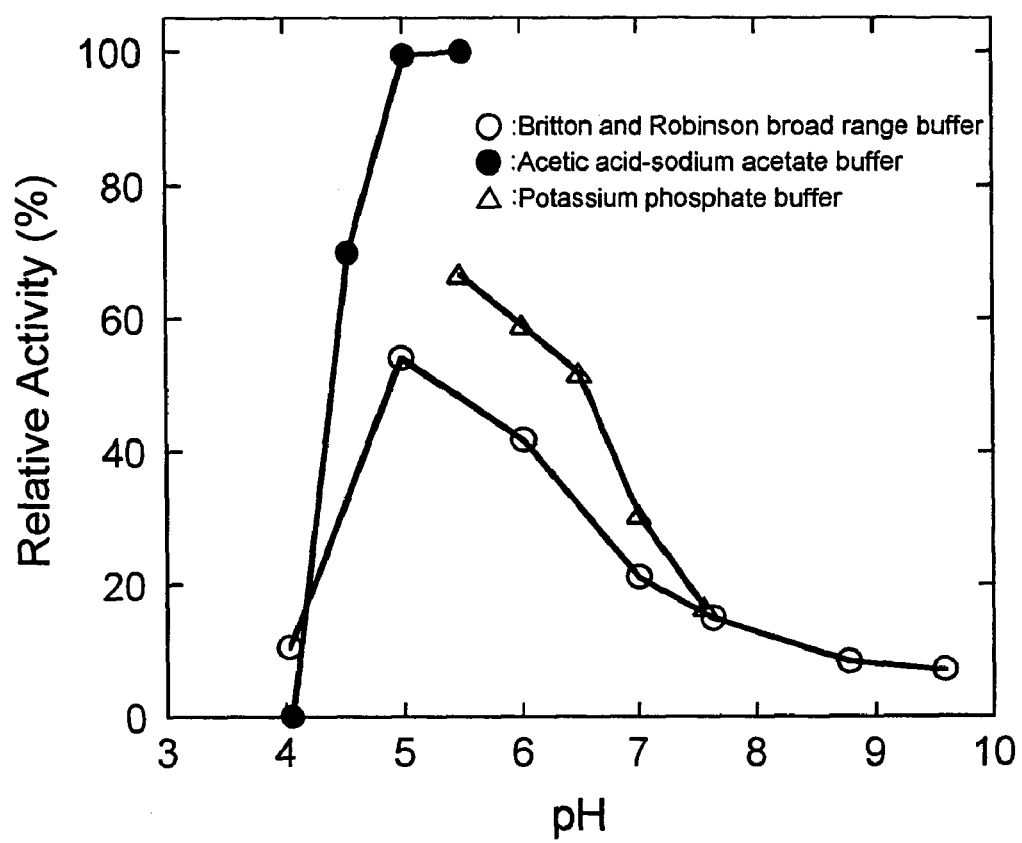
FIG. 2 depicts a diagram showing the pH dependency of the 2-chlorophenyl glyoxylic acid-reducing activity of the enzyme obtained in Example 9. The ordinate indicates the relative enzymatic activity (%) taking the maximal activity as 100%; the abscissa indicates the pH.

2-chlorophenyl glyoxylic acid-reducing activities of the enzyme obtained in Example 9 at various pHs were determined by changing the pH with the use of potassium phosphate buffer, sodium acetate buffer, and Britten and Robinson broad-range buffer. The activities are shown in FIG. 2, defined as relative activities taking the maximal activity as 100. The optimum pH for the reaction was 5.0 to 5.5.

EXAMPLE 12

Figure 3:
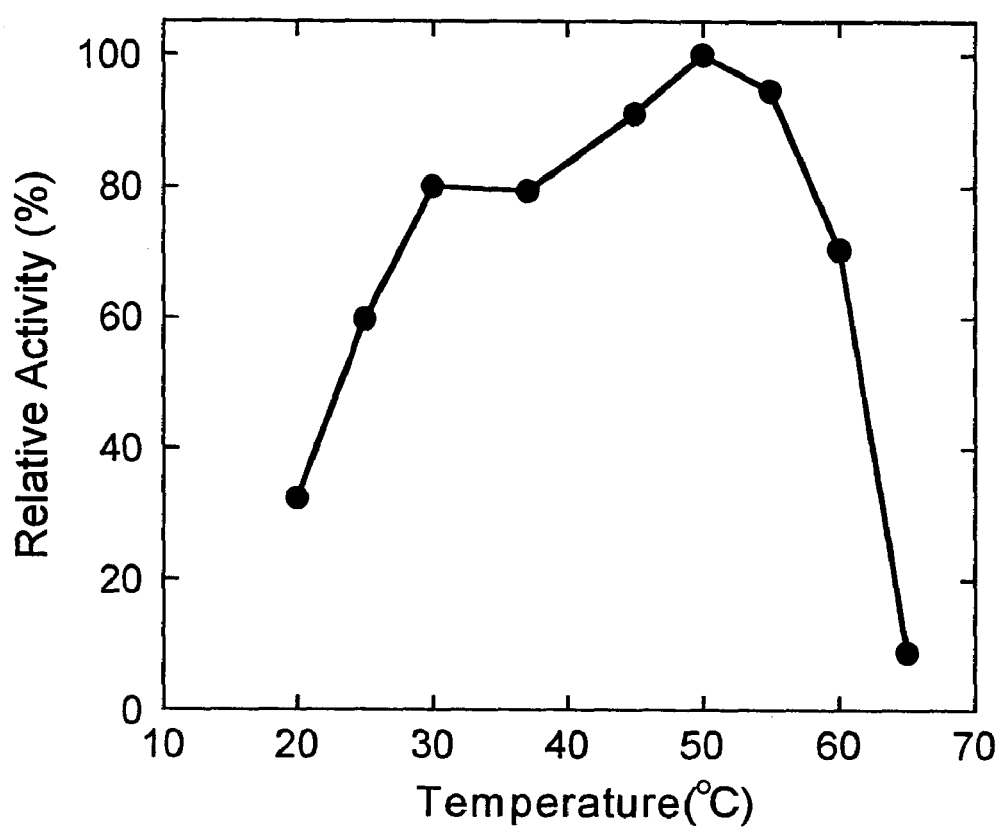
FIG. 3 depicts a diagram showing the temperature dependency of the 2-chlorophenyl glyoxylic acid-reducing activity of the enzyme obtained in Example 9. The ordinate indicates the relative enzymatic activity (%) taking the maximal activity as 100%; the abscissa indicates the temperature (° C.).

Optimum Temperature of α-keto Acid Reductase 2-chlorophenyl glyoxylic acid-reducing activities of the enzyme obtained in Example 9 were measured under standard reaction conditions at various temperatures. The activities are shown in FIG. 3, defined as relative activities taking the maximal activity as 100. The activity was 80% or higher of the maximal activity at a temperature of 45° C. to 55° C.

EXAMPLE 13 pH Stability of α-keto Acid Reductase

Figure 4:
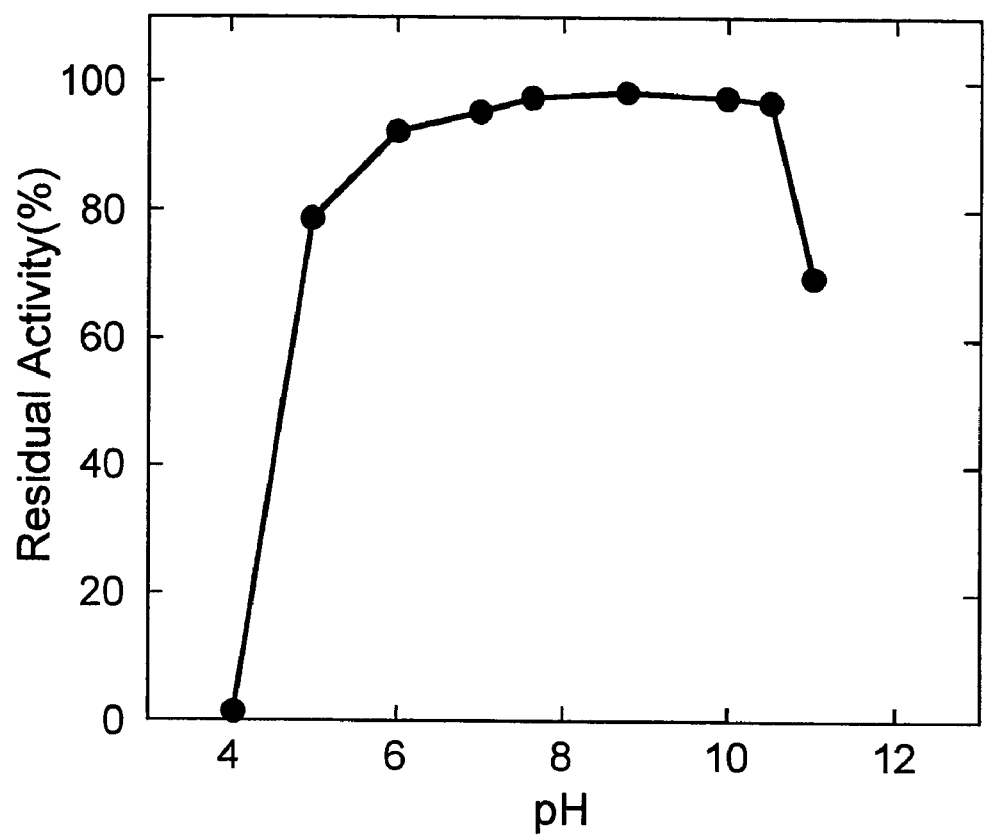
FIG. 4 depicts a diagram showing the pH stability of the 2-chlorophenyl glyoxylic acid-reducing activity of the enzyme obtained in Example 9. The ordinate indicates the relative enzymatic activity (%) taking the maximal activity as 100%; the abscissa indicates the pH.

The enzyme obtained in Example 9 was incubated in Britten and Robinson broad-range buffer at 25° C. for 30 minutes, and residual 2-chlorophenyl glyoxylic acid-reducing activities were determined. The residual activities are shown in FIG. 4, defined by taking the activity of untreated sample as 100. The residual activities were 80% or higher at pH 5 to 10.5.

EXAMPLE 14

Thermostability of α-keto Acid Reductase

Figure 5:
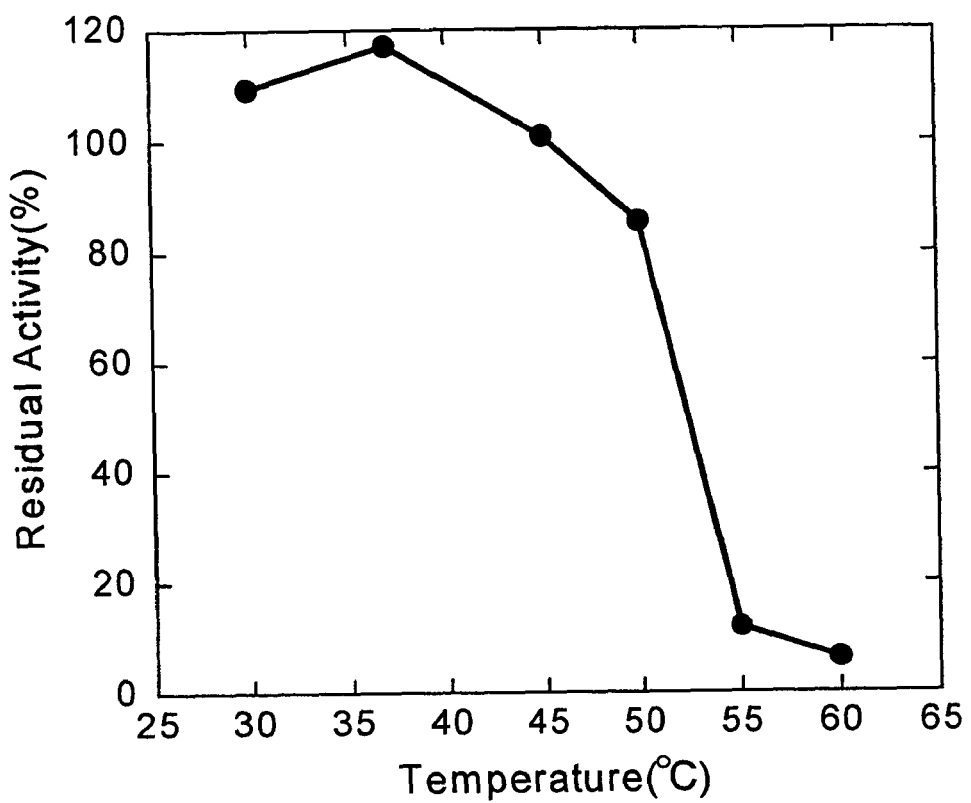
FIG. 5 depicts a diagram showing the thermostability of the 2-chlorophenyl glyoxylic acid-reducing activity of the enzyme obtained in Example 9. The ordinate indicates the relative enzymatic activity (%) taking the maximal activity as 100; the abscissa indicates the temperature (° C.).

The enzyme obtained in Example 9 was incubated in potassium phosphate buffer (pH 8.0) at various temperatures for 10 minutes, and residual 2-chlorophenyl glyoxylic acid-reducing activities were determined. The residual activities are shown in FIG. 5, defined by taking the activity of untreated sample as 100. The residual activity was 80% or higher at the temperature of 50° C. or lower.

EXAMPLE 15

Substrate Specificity of α-keto Acid Reductase

The enzyme obtained in Example 9 was incubated with various α-keto acids, ketones, ketols, etc. The activities of the reduction reaction are shown in Table 8, defined as relative activities taking the reduction activity of 2-chlorophenyl glyoxylic acid as 100.

TABLE 8

Substrate specificity of α-keto acid reductase

| Substrate | Coenzyme | Concentration (mM) | Relative activity (%) |
|---|---|---|---|
| 2-chlorophenyl glyoxylic acid | NADH | 1 | 100.0 |
| 2-chlorophenyl glyoxylic acid | NADPH | 1 | 0.4 |
| pyruvic acid | NADH | 1 | 0.0 |
| α-ketobutyric acid | NADH | 1 | 0.4 |
| α-ketovaleric acid | NADH | 1 | 3.1 |
| α-ketocaproic acid | NADH | 1 | 4.3 |
| keto pantoic acid | NADH | 5 | 3.1 |
| α-ketoisovaleric acid | NADH | 1 | 19.3 |
| α-ketoisocaproic acid | NADH | 1 | 14.7 |
| trimethyl pyruvic acid | NADH | 1 | 0.1 |
| phenyl glyoxylic acid | NADH | 1 | 12.9 |
| β-phenylpyruvic acid | NADH | 1 | 0.3 |
| α-keto-4-phenylpyruvic acid | NADH | 1 | 0.1 |
| 3-chlorophenyl glyoxylic acid | NADH | 1 | 4.5 |
| (R,S)-2-chloromandelic acid | NAD$^+$ | 1 | 0.022 |
| (R)-2-chloromandelic acid | NAD$^+$ | 1 | 0.045 |

EXAMPLE 16

Synthesis of (R)-2-chloromandelic Acid Using α-keto Acid Reductase

A reaction solution containing 200 mM potassium phosphate buffer (pH 6.5), 100 mM NADH, 1U α-keto acid reductase, and 50 mM 2-chlorophenyl glyoxylic acid was incubated at 25° C. overnight. The resulting 2-chloromandelic acid was quantified and its optical purity was determined according to the procedure of Example 2. As a result, the 2-chloromandelic acid generated according to the present invention was the R isomer with an optical purity of 99% ee. The reaction yield was 100%.

EXAMPLE 17

Partial Amino Acid Sequence of α-keto Acid Reductase

The N-terminal amino acid sequence of the enzyme obtained in Example 9 was analyzed using protein sequencer. The amino acid sequence is shown in SEQ ID NO: 3. A piece of the SDS-PAGE gel containing α-keto acid reductase was excised. After washing the gel twice, in-gel digestion was carried out overnight at 35° C. using lysyl-endopeptidase. The digested peptides were fractionated using reverse-phase HPLC (TSK gel ODS-80-Ts, 2.0 mm×250 mm; Tosoh Corp.) by a gradient elution with acetonitrile in 0.1% trifluoro acetic acid to obtain peptides.

Two of the fractionated peptide peak fractions were designated as "lep__71" and "lep__72", respectively, and their amino acid sequences were analyzed with protein sequencer (Hewlett Packard G1005A Protein Sequencer System). The amino acid sequences of lep__71 and lep__72 are shown in SEQ ID NOs: 4 and 5, respectively.

Met-Lys-Ile-Ala-Ile-Ala-Gly-Phe-Gly-Ala-Leu-Gly-Ala-Arg-Leu    SEQ ID NO:3/N-terminal amino acid sequence Leu-Gly-Val-Met-Leu-Gln-Ala-Gly-Gly-His    SEQ ID NO:4/lep_71

Thr-Glu-Ile-Asp-Phe-Leu-Asn-Gly-Tyr-Phe    SEQ ID NO:5/lep_72

EXAMPLE 18

Purification of Chromosomal DNA from *Leuconostoc mesenteroides* subsp. *dextranicum*

*Leuconostoc mesenteroides* subsp. *dextranicum* strain (ATCC 17072) was cultured in MRS medium, and then the cells were harvested. The chromosomal DNA of the cells was purified according to the method described in J. Dairy Sci., 75, 1186–1191 (1992).

EXAMPLE 19

Cloning of the Core Region of α-keto Acid Reductase

Sense primers and antisense primers were synthesized based on the amino acid sequences of the N-terminus, lep_71, and lep_72. Respective nucleotide sequences of the primers are shown in SEQ ID NO: 6 (LmKAR-N4), SEQ ID NO: 7 (LmKAR-71B), SEQ ID NO: 8 (LmKAR-71D), SEQ ID NO: 9 (LmKAR-72B) and SEQ ID NO: 10 (LmKAR-72D).

```
                    SEQ ID NO:6/LmKAR-N4
CTGAAGCTTATGAARATHGCHATHGCNGG

SEQ ID NO:7/LmKAR-71B
CAGAAGCTTTGDCCDCCDGCYTGYARCATNAC

SEQ ID NO:8/LmKAR-71D
CTGAAGCTTGGYGTHATGYTDCARGCHGGNGG

SEQ ID NO:9/LmKAR-72B
GTCAAGCTTTADCCRTTYARRAARTCDATYTC

SEQ ID NO:10/LmKAR-72D
CTGAAGCTTACHGARATYGAYTTYYTDAAYGG
```

The five primers were combined as four pairs: LmKAR-N4 and LmKAR-71B; LmKAR-N4 and LmKAR-72B; LmKAR-71D and LmKAR-72B; and LmKAR-72D and LmKAR-71B. PCR was carried out using a reaction solution (50 μL) containing each of the pair of primers (50 pmol each of the primer), 10 nmol dNTP, 50 ng chromosomal DNA derived from *Leuconostoc mesenteroides* subsp. *dextranicum*, Ex-Taq buffer (TaKaRa Shuzo Co., Ltd.), and Ex-Taq 2U (TaKaRa Shuzo Co., Ltd.) on GeneAmp PCR System 2400 (Perkin Elmer). The PCR condition was as follows: 30 cycles of denaturation at 94° C. for 30 seconds, annealing at 50° C. for 30 seconds, and extension at 70° C. for 40 seconds.

An aliquot of the PCR reaction solution was analyzed by agarose gel electrophoresis. A seemingly specific band of approximately 800 bp was detected with the pairs of primers, LmKAR-N4 and LmKAR-71B, and LmKAR-71D and LmKAR-72B. After extracting the two DNA fragments with phenol/chloroform, the fragments were collected as ethanol-precipitation and digested with restriction enzyme HindIII. Then, agarose gel electrophoresis was conducted to excise the band of interest from the gel and purify by Sephaglas BandPrep Kit (Pharmacia).

The obtained DNA fragment was ligated using TaKaRa Ligation Kit with pUC18 (TaKaRa Shuzo Co., Ltd.), which was pre-digested with HindIII. The ligated DNA was then transformed into *E. coli* strain JM109.

The transformant was grown on LB medium plate (1% bacto-tryptone, 0.5% bacto-yeast extract, 1% sodium chloride; hereinafter abbreviated as LB medium) containing ampicillin (50 μmL). Several white colonies selected by the Blue/White selection method were cultured in liquid LB medium containing ampicillin. Plasmids were purified by Flexi-Prep (Pharmacia). The plasmid containing the DNA fragment amplified by the combination of LmKAR-N4 and LmKAR-72B was dubbed "pLMK1", and the plasmid containing the DNA fragment amplified by the combination of LmKAR-71D and LmKAR-72B was dubbed "pLMK2."

The nucleotide sequence of the insert DNA was analyzed using the purified plasmids. The nucleotide sequence analysis was carried out by PCR using BigDye Terminator Cycle Sequencing FS ready Reaction Kit (Perkin Elmer) on DNA sequencer ABI PRISM™ 310 (Perkin Elmer). The determined nucleotide sequence of the core region is shown in SEQ ID NO: 11.

EXAMPLE 20

Analysis of Nucleotide Sequence Flanking the Core Region of α-keto Acid Reductase Gene Chromosomal DNA derived from *Leuconostoc mesenteroides* subsp. *dextranicum* was digested with restriction enzymes PstI and HaeII, and each of the digested fragments was cyclized overnight at 16° C. by self-ligation using T4 ligase. Then, PCR was carried out in 50 μL of a reaction solution containing LA-Taq buffer (TaKaRa Shuzo Co., Ltd.) and LA-Taq 2U (TaKaRa Shuzo Co., Ltd.) using primers: LMK-IPU (SEQ ID NO: 12) and LMK-IPD (SEQ ID NO: 13) (100 pmol each), and 25 ng of the cyclized DNA on GeneAmp PCR System 2400 (Perkin Elmer). The condition for the PCR was: 30 cycles of denaturation at 94° C. for 30 seconds, annealing at 55° C. for 30 seconds and extension at 72° C. for 10 minutes. An aliquot of the PCR solution was analyzed by agarose gel electrophoresis. Digestion of the template DNA with PstI and HaeII yielded DNA fragments of approximately 2500 bp and 4000 bp. The DNA fragments were purified by Sephaglas BandPrep Kit (Pharmacia) and the nucleotide sequences were analyzed using LMK-IPU and LMK-IPD. The open reading frame (ORF) sequence of the α-keto acid reductase was thus determined. The determined DNA sequence is shown in SEQ ID NO: 1 and the deduced amino acid sequence is shown in SEQ ID NO: 2. ORF search was carried out using Genetyx-win software (Software Development Co., Ltd.).

```
TCACTTGCCGGCATAACTGG        SEQ ID NO:12/LMK-IPU

GTCACAAGGCATTAAAGTTGACG     SEQ ID NO:13/LMK-IPD
```

EXAMPLE 21

Cloning of α-keto Acid Reductase

Primers LmKAR-N5 (SEQ ID NO: 14) and LmKAR-C (SEQ ID NO: 15) were synthesized to clone a fragment containing only the ORF from the structural gene sequence of α-keto acid reductase. PCR was carried out in 50 μL of a reaction solution containing a set of primers (50 pmol each), 10 nmol dNTP, 50 ng chromosomal DNA derived from *Leuconostoc mesenteroides* subsp. *dextranicum*, Pfu Turbo-DNA polymerase buffer (STRATAGENE), and 3.75 U Pfu Turbo-DNA polymerase (STRATAGENE) on Gene-Amp PCR System 2400 (Perkin Elmer). The condition for the PCR was: 30 cycles of denaturation at 95° C. for 2 minutes and 30 seconds, annealing at 55° C. for 1 minute and extension at 72° C. for 1 minute.

```
                                    SEQ ID NO:14/LmKAR-N5
GTCGAATTCTATCATGAAAATTGCAATTGCAGGATTTGGTGCAC

SEQ ID NO:15/LmKAR-C
GATAAGCTTACTAGTATTAAATTTCAAAGTTTTCTTGCTGTTTTGCTAAT
TTAACACG
```

The amplified DNA fragment was extracted with phenol/chloroform and collected as an ethanol-precipitate. Then, the collected DNA fragment was double-digested with restriction enzymes EcoRI and HindIII. Agarose gel electrophoresis was conducted to excise the bands of interest from the gel and purify with Sephaglas BandPrep Kit (Pharmacia).

The purified DNA fragment was ligated using TaKaRa Ligation Kit with pSE420D, which was double-digested with EcoRI and HindIII. pSE420D is a plasmid prepared by modifying the multi-cloning site of plasmid vector pSE420 (Invitrogen; JP-A 2000-189170). The resulting plasmid was transformed into *E. coli* strain JM109.

Figure 6:
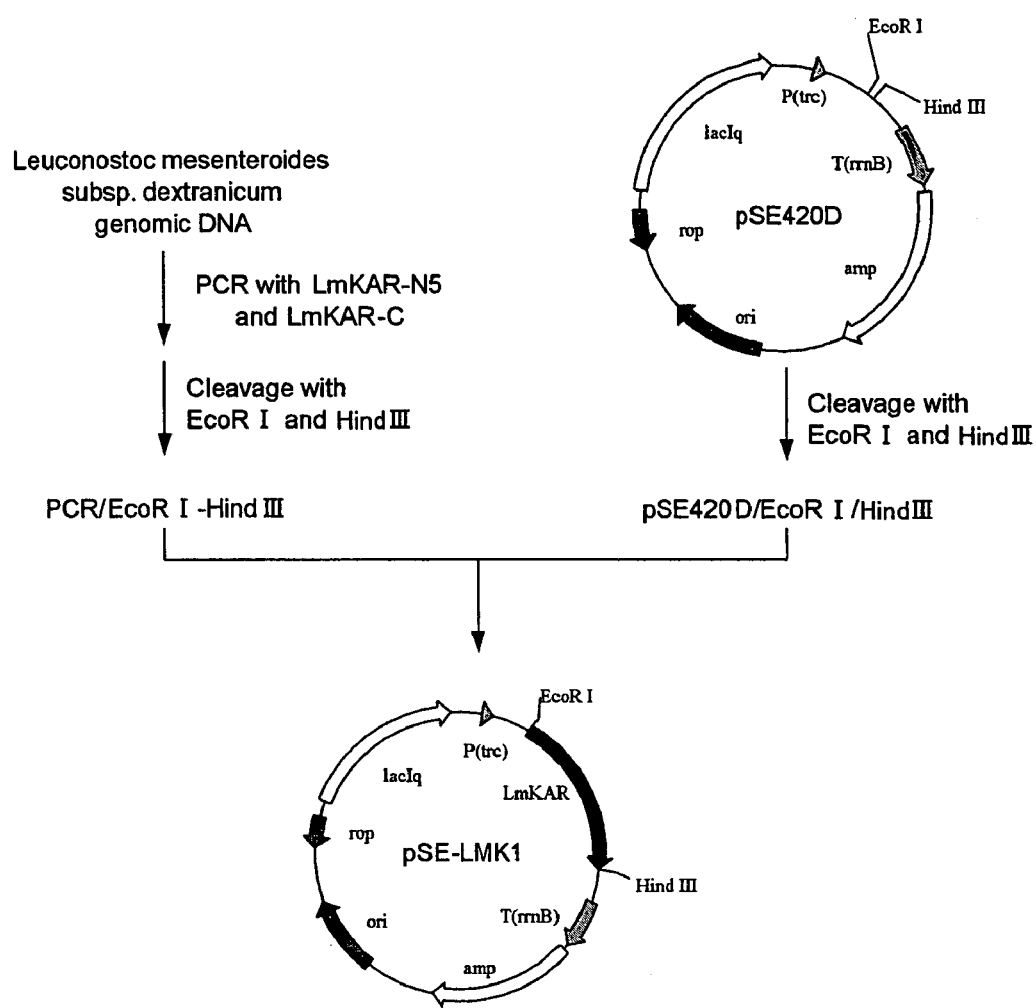
FIG. 6 depicts a schematic illustration of the construction of the plasmid pSE-LMK1, which contains as an insert the α-keto acid reductase derived gene from *Leuconostoc mesenteroides* subsp. *dextranicum*. In the plasmid map, P(trc) indicates the trc promoter; T(rrnB), the rrnBT1T2 terminator; amp, the β-lactase gene for ampicillin resistance; ori, the replication origin of the plasmid; rop, the ROP-protein gene; and laqIq, the lactose repressor. LmKAR of pSE-LMK1 indicates the α-keto acid reductase gene derived from *Leuconostoc mesenteroides* subsp. *dextranicum*.

The transformant was grown on LB medium plate containing ampicillin. The nucleotide sequence of the insert fragment was determined. The plasmid encoding the α-keto acid reductase gene of interest was dubbed "pSE-LMK1". The procedure of plasmid construction is shown in FIG. 6.

EXAMPLE 22

Production of α-keto Acid Reductase by *E. coli*

The *E. coli* strain JM109 transformed with the plasmid pSE-LMK1 expressing α-keto acid reductase was cultured overnight at 30° C. in liquid LB medium containing ampicillin. Then, 0.1 mM isopropyl-1-thio-β-D-galactoside (IPTG) was added and the culture was further continued for four hours.

Bacterial cells were harvested by centrifugation and suspended in 50 mM Tris-HCl buffer (pH 8.5) containing 0.02% 2-mercaptoethanol, 2 mM PMSF and 10% glycerin. The cells were lysed by sonication in Bioruptor UCD-200™ (Cosmo Bio) for 3 minutes. The bacterial cell lysate was centrifuged and the resulting supernatant was collected as bacterial extract. *E. coli* containing the plasmid pSE420D (control) without the α-keto acid reductase gene was also cultured overnight in LB medium. After the addition of 0.1 mM IPTG, cells were further cultured for four hours. The cells were also crushed by the same procedure as described above, and then used in assay for 2-chlorophenyl glyoxylic acid-reducing activity. The result is shown in Table 9.

TABLE 9

Effect of the plasmids

| Plasmid | 2-chlorophenyl glyoxylic acid-reducing activity (U/mg protein) |
|---|---|
| pSE420D (control) | 0 |
| pSE-LMK1 | 383 |

EXAMPLE 23

Figure 7:
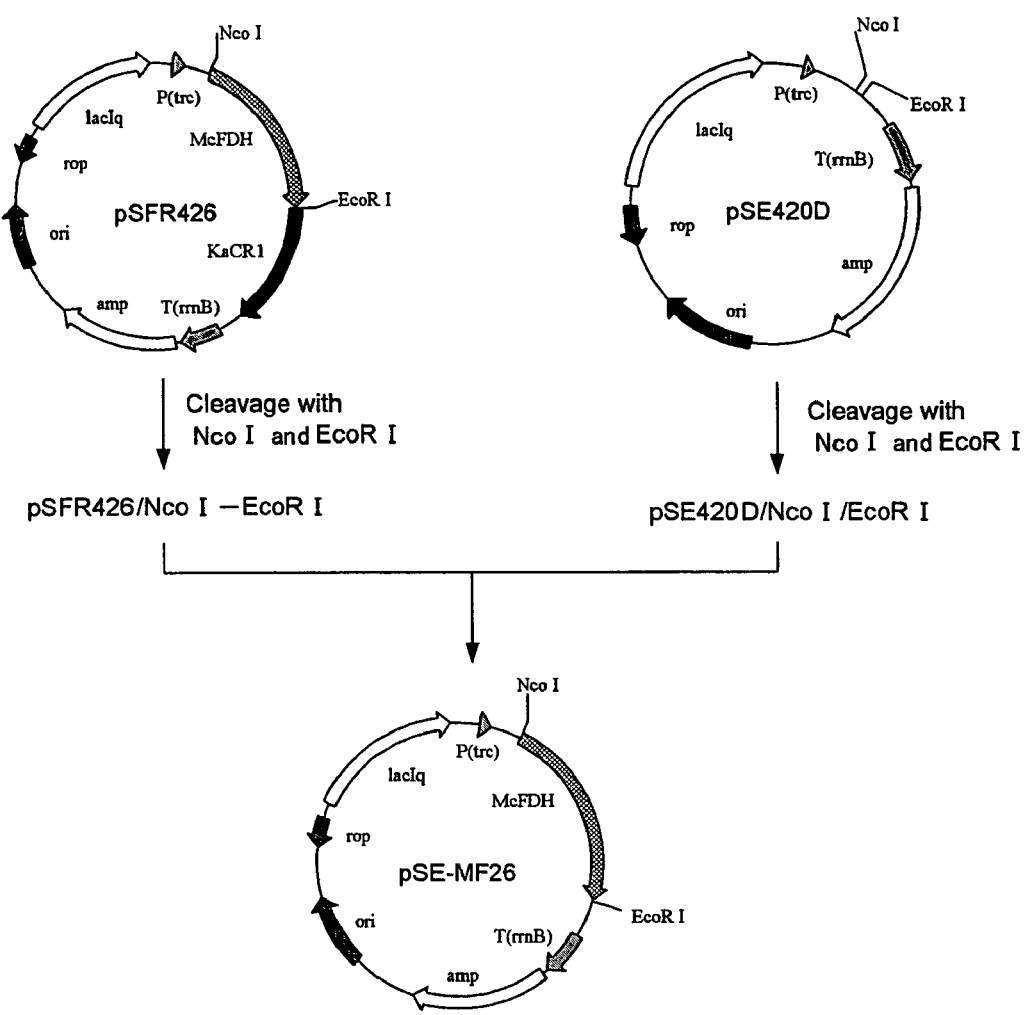
FIG. 7 depicts a schematic illustration of the construction of the plasmid pSE-MCF26, which contains as an insert the formate dehydrogenase gene derived from *Mycobacterium vaccae*. In the plasmid map, P(trc) indicates the trc promoter; T(rrnB), the rrnBT1T2 terminator; amp, the β-lactase gene for ampicillin resistance; ori, the replication origin of the plasmid; rop, the ROP-protein gene; laqIq, the lactose repressor; and McFDH, the formate dehydrogenase gene derived from *Mycobacterium vaccae*.
Figure 8:
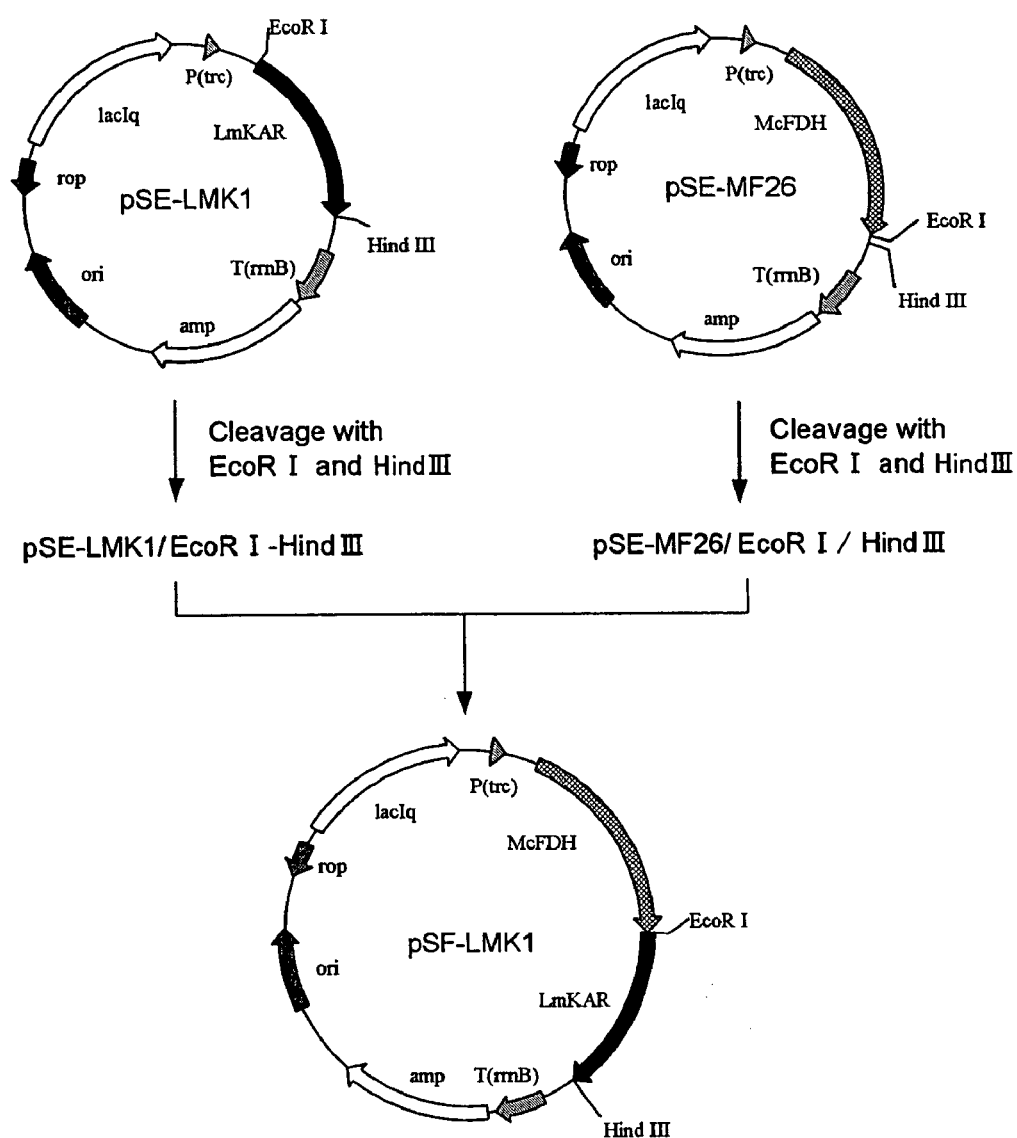
FIG. 8 depicts a schematic illustration of the construction of the plasmid pSF-LMK1, which contains as inserts the *Leuconostoc mesenteroides* subsp. *dextranicum*-derived α-keto acid reductase and the *Mycobacterium vaccae*-derived formate dehydrogenase gene. In the plasmid map, P(trc) indicates the trc promoter; T(rrnB), the rrnBT1T2 terminator; amp, the β-lactase gene for ampicillin resistance; ori, the replication origin of plasmid; rop, ROP-protein gene; laqIq, the lactose repressor; McFDH, the formate dehydrogenase gene derived from *Mycobacterium vaccae*; and LmKAR, the α-keto acid reductase gene derived from *Leuconostoc mesenteroides* subsp. *dextranicum*.

Construction of Plasmid pSF-LMK1 for Co-expression of α-keto Acid Reductase and Mycobacterium-derived Formate Dehydrogenase Genes Plasmid pSFR426 (EP 1211316) expressing the Mycobacterium-derived formate dehydrogenase gene was double-digested with restriction enzymes NcoI and EcoRI to prepare a DNA fragment containing the Mycobacterium-derived formate dehydrogenase gene. The prepared DNA fragment was ligated using TaKaRa Ligation Kit with pSE420D, which was double-digested with NcoI and EcoRI. The resulting plasmid was transformed into *E. coli* strain JM109. The transformant was cultured in liquid LB medium containing ampicillin. The plasmid was purified with Qiagen Tip-500 (QIAGEN). The plasmid containing the DNA fragment of the Mycobacterium-derived formate dehydrogenase gene was dubbed "pSE-MF26". The procedure of plasmid construction is shown in FIG. 7.

pSE-MF26 was double-digested with two restriction enzymes EcoRI and HindIII, and then, using TaKaRa Ligation Kit, ligated with a DNA fragment containing the α-keto acid reductase gene digested from pSE-LMK1 with the same enzymes. The obtained plasmid co-expresses the formate dehydrogenase and α-keto acid reductase and was dubbed "pSF-LMK1". The procedure of plasmid construction is shown in FIG. 8.

EXAMPLE 24

Co-expression of α-keto Acid Reductase and Formate Dehydrogenase in *E. coli*

*E. coli* strain JM109 was transformed with pSF-LMK1 and cultured overnight at 30° C. in liquid LB medium containing ampicillin. 0.1 mM IPTG was added and the culture was incubated for another 4 hours.

Bacterial cells were harvested by centrifugation, suspended in 50 mM Tris-HCl buffer (pH 8.5) containing 0.02% 2-mercaptoethanol, 2 mM PMSF and 10% glycerin, and lysed by sonication in Bioruptor UCD-200™ (Cosmo Bio) for 3 minutes. The bacterial cell lysate was centrifuged and the resulting supernatant was collected as bacterial extract. The extract was assayed for its activities to reduce 2-chlorophenyl glyoxylic acid and dehydrogenate formate. Assay for the formate dehydrogenase activity was carried out at 30° C. in a reaction solution containing 100 mM potassium phosphate buffer (pH 7.0), 2.5 mM $NAD^+$, 100 mM formic acid, and the enzyme. 1 U was defined as an enzyme quantity which catalyzes the production of 1 μmol NADH in 1 minute under the reaction condition described above. The crude enzyme liquid derived from *E. coli* was determined to have a 2-chlorophenyl glyoxylic acid-reducing activity of 620 U/mg protein and a formate dehydrogenase activity of 0.240 U/mg protein.

EXAMPLE 25

Production of (R)-2-chloromandelic acid Using *E. coli* strain HB101 Transformed with pSF-LMK1

The *E. coli* strain HB101 transformed with pSF-LMK1 was cultured overnight at 30° C. in 20 mL of liquid LB medium containing ampicillin. Then 0.1 mM IPTG was added to the culture and the cells were further cultured for four hours.

Bacterial cells were harvested by centrifugation, and suspended in 10 mL of 500 mM potassium phosphate buffer (pH 6.5) containing 270 mM 2-chlorophenyl glyoxylic acid and 540 mM sodium formate. The suspension was reacted with shaking at 30° C. overnight. After the reaction, the optical purity of the generated 2-chloromandelic acid, and the quantities of 2-chloromandelic acid and 2-chlorophenyl glyoxylic acid in the reaction solution were determined similar to the analysis methods in Example 2. The optical purity of the generated (R)-2-chloromandelic acid was higher than 99% ee, and the reaction yield was 100%.

EXAMPLE 26

Construction of Plasmid pSG-LMK1 Co-expressing α-keto Acid Reductase Gene and Glucose Dehydrogenase Gene Derived from *Bacillus subtilis*

Figure 9:
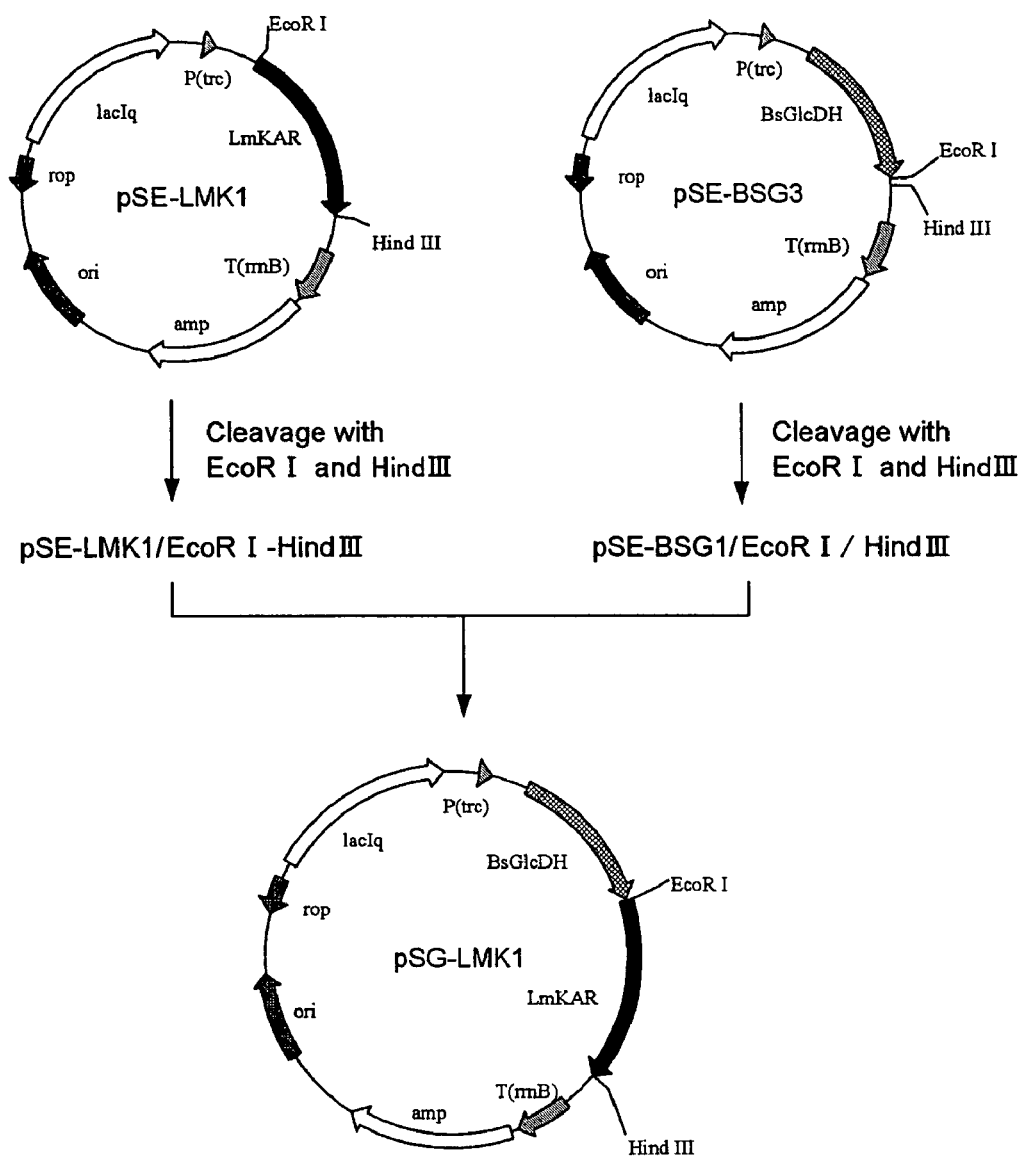
FIG. 9 depicts a schematic illustration of the construction of the plasmid pSG-LMK1, which contains as inserts the *Leuconostoc mesenteroides* subsp. *dextranicum*-derived α-keto acid reductase and the *Bacillus subtilis*-derived glucose dehydrogenase gene. In the plasmid map, P(trc) indicates the trc promoter; T(rrnB), rrnBT1T2 terminator; amp, the β-lactase gene for ampicillin resistance; ori, the replication origin of plasmid; rop, the ROP-protein gene; laqIq, the lactose repressor; BsGlcDH, the glucose dehydrogenase gene derived from *Bacillus subtilis*; and LmKAR, the α-keto acid reductase gene derived from *Leuconostoc mesenteroides* subsp. *dextranicum*.

Plasmid pSE-BSG3 (JP-A 2000-3745931) containing the glucose dehydrogenase gene derived from *Bacillus subtilis* was double-digested with two restriction enzymes EcoRI and HindIII, and ligated, using TaKaRa Ligation Kit, with a DNA fragment containing the α-keto acid reductase gene digested from pSE-LMK1 with the same enzymes. Thus, a plasmid co-expressing the glucose dehydrogenase and α-keto acid reductase was obtained and dubbed "pSG-LMK1". The procedure of plasmid construction is shown in FIG. 9.

EXAMPLE 27

Co-expression of α-keto Acid Reductase and Glucose Dehydrogenase in *E. coli*

*E. coli* strain JM109 was transformed with pSG-LMK1 and cultured overnight at 30° C. in liquid LB medium containing ampicillin. 0.1 mM IPTG was added and the culture was continued for another 4 hours.

Bacterial cells were harvested by centrifugation, suspended in 50 mM potassium phosphate buffer (pH 6.5) containing 0.5M NaCl, 0.02% 2-mercaptoethanol, 2 mM PMSF and 10% glycerin, and lysed by sonication in a Bioruptor UCD-200™ (Cosmo Bio) for 3 minutes. The bacterial cell lysate was centrifuged and the resulting supernatant was collected as bacterial extract. The extract was assayed for its activities to reduce 2-chlorophenyl glyoxylic acid and dehydrogenate glucose. The assay for glucose dehydrogenase activity was carried out in a reaction solution containing 100 mM potassium phosphate buffer (pH 6.5), 2.5 mM $NAD^+$, 100 mM glucose, and the enzyme at 30° C. 1 U was defined as an enzyme quantity which catalyzes the production of 1 μmol NADH in 1 minute under the reaction condition described above. The crude enzyme liquid derived from *E. coli* was determined to have a 2-chlorophenyl glyoxylic acid-reducing activity of 800 U/mg protein, and a glucose dehydrogenase activity of 5.87 U/mg protein.

EXAMPLE 28

Production of (R)-2-chloromandelic acid Using *E. coli* Strain HB101 Transformed with pSG-LMK1

*E. coli* strain HB101 was transformed with pSG-LMK1, and cultured overnight at 30 ° C. in 20 mL of liquid LB medium containing ampicillin. Then, 0.1 mM IPTG was added for further culture for four hours.

Bacterial cells were harvested by centrifugation, suspended in 10 mL of 500 mM potassium phosphate buffer (pH 7.5) containing 270 mM 2-chlorophenyl glyoxylic acid and 324 mM glucose, and the suspension was reacted overnight with shaking at 30° C. After the reaction, the optical purity of the generated 2-chloromandelic acid and the quantities of 2-chloromandelic acid and 2-chlorophenyl glyoxylic acid in the reaction solution were determined similarly to the analysis methods shown in Example 2. The optical purity of the generated (R)-2-chloromandelic acid was higher than 99% ee, and the reaction yield was 70%.

While the invention has been described in detail and with reference to specific embodiments thereof, it will be apparent to one skilled in the art that various changes and modifications can be made therein without departing from the spirit and scope of the invention.

What is claimed is:

1. An isolated α-keto acid reductase having the following physicochemical properties:
   (i) function:
      reduces α-keto acid to (R)-α-hydroxy acid using reduced β-nicotinamide adenine dinucleotide as the coenzyme; and
   (ii) substrate specificity:
      (a) utilizes reduced β-nicotinamide adenine dinucleotide as the coenzyme in the reduction reaction of (i);
      (b) reduces 2-chlorophenyl glyoxylic acid to (R)-2-chloromandelic acid; and
      (c) reduces 2-chlorophenyl glyoxylic acid but the dehydrogenase activity of said α-keto acid reductase against either of the two optical isomers of 2-chloromandelic acid is no more than 20% taking the relative activity of said α-keto acid reductase to reduce 2-chlorophenyl glyoxylic acid,
   wherein said α-keto acid reductase is encoded by a polynucleotide selected from the group consisting of:
      (1) a polynucleotide comprising the nucleotide sequence of SEQ ID NO:1;
      (2) a polynucleotide encoding a protein comprising the amino acid sequence of SEQ ID NO:2; and
      (3) a polynucleotide encoding an amino acid sequence comprising an amino acid sequence at least 95% homologous to the amino acid sequence of SEQ ID NO:2.

2. The isolated α-keto acid reductase of claim 1, further having the following physicochemical properties:
   (iii) optimum pH:
      pH 5.0 to 5.5;
   (iv) optimum temperature:
      45 to 550° C.; and
   (v) molecular weight of
      about 35,000 Daltons and about 63,000 Daltons, as determined by sodium dodecyl sulfate-polyacrylamide gel electrophoresis and gel filtration, respectively.

3. The isolated α-keto acid reductase of claim 1, which is produced by a microorganism belonging to the genus *Leuconostoc*.

4. The isolated α-keto acid reductase of claim 3, wherein the microorganism belonging to the genus *Leuconostoc* is *Leuconostoc mesenteroides*.

5. The isolated α-keto acid reductase of claim 4, wherein the microorganism belonging to *Leuconostoc mesenteroides* is *Leuconostoc mesenteroides* subsp. *dextranicum*.

6. An isolated protein, wherein said protein is an enzyme that catalyzes the reduction of α-keto acids, and wherein said protein is encoded by a polynucleotide selected from the group consisting of:
   (1) a polynucleotide comprising the nucleotide sequence of SEQ ID NO:1; and
   (2) a polynucleotide encoding a protein comprising the amino acid sequence of SEQ ID NO:2.

* * * * *

UNITED STATES PATENT AND TRADEMARK OFFICE
CERTIFICATE OF CORRECTION

PATENT NO. : 7,250,278 B2  Page 1 of 1
APPLICATION NO. : 10/619779
DATED : July 31, 2007
INVENTOR(S) : Norihiro Kimoto et al.

It is certified that error appears in the above-identified patent and that said Letters Patent is hereby corrected as shown below:

Column 14, line number 55, please replace "pAM ☐ 1" with --pAM β1--.
Column 31, line 1, please replace
"Met-Lys-Ile-Ala-Ile-Ala-Gly-Phe-Gly-Ala-Leu-Gly-Ala-Arg-Leu
Leu-Gly-Val-Met-Leu-Gln-Ala-Gly-Gly-His
Thr-Glu-Ile-Asp-Phe-Leu-Asn-Gly-Tyr-Phe" with
-- SEQ ID NO: 3/N-terminal amino acid sequence
Met-Lys-Ile-Ala-Ile-Ala-Gly-Phe-Gly-Ala-Leu-Gly-Ala-Arg-Leu
SEQ ID NO: 4/lep_71
Leu-Gly-Val-Met-Leu-Gln-Ala-Gly-Gly-His
SEQ ID NO: 5/lep_72
Thr-Glu-Ile-Asp-Phe-Leu-Asn-Gly-Tyr-Phe--.
Column 46, line 33, please replace "550°C" with -- 55°C --.

Signed and Sealed this

Eighteenth Day of December, 2007

JON W. DUDAS
*Director of the United States Patent and Trademark Office*

SEQUENCE LISTING

<160> NUMBER OF SEQ ID NOS: 15

<210> SEQ ID NO 1
<211> LENGTH: 954
<212> TYPE: DNA
<213> ORGANISM: Leuconostoc mesenteroides
<220> FEATURE:
<221> NAME/KEY: CDS
<222> LOCATION: (1)..(954)

<400> SEQUENCE: 1

```
atg aaa ata gct att gca gga ttt ggt gca ctt ggt gca cga tta ggt    48
Met Lys Ile Ala Ile Ala Gly Phe Gly Ala Leu Gly Ala Arg Leu Gly
```

-continued

|  |  |  |  |  |  |  |  |  |  |  |  |  |  |  |  |  |
|---|---|---|---|---|---|---|---|---|---|---|---|---|---|---|---|---|
| 1 |  |  |  | 5 |  |  |  |  | 10 |  |  |  |  | 15 |  |  |

| gtc | atg | ctc | cag | gct | ggt | ggc | cat | gag | gtt | acc | ggg | att | gat | ggt | tgg | 96 |
|---|---|---|---|---|---|---|---|---|---|---|---|---|---|---|---|---|
| Val | Met | Leu | Gln | Ala | Gly | Gly | His | Glu | Val | Thr | Gly | Ile | Asp | Gly | Trp | |
|  |  |  | 20 |  |  |  |  | 25 |  |  |  |  | 30 |  |  |  |

| ccg | gca | cat | att | gct | gct | att | aat | aca | aaa | ggt | tta | aca | gtc | gtt | aaa | 144 |
|---|---|---|---|---|---|---|---|---|---|---|---|---|---|---|---|---|
| Pro | Ala | His | Ile | Ala | Ala | Ile | Asn | Thr | Lys | Gly | Leu | Thr | Val | Val | Lys | |
|  |  | 35 |  |  |  |  | 40 |  |  |  |  | 45 |  |  |  |  |

| gat | aat | gat | gca | cca | caa | aag | tat | ttt | gta | cca | gtt | atg | ccg | gca | agt | 192 |
|---|---|---|---|---|---|---|---|---|---|---|---|---|---|---|---|---|
| Asp | Asn | Asp | Ala | Pro | Gln | Lys | Tyr | Phe | Val | Pro | Val | Met | Pro | Ala | Ser | |
| 50 |  |  |  |  | 55 |  |  |  |  | 60 |  |  |  |  |  |  |

| gaa | gtg | aca | ggc | aca | ttt | gat | tta | att | att | tta | ctc | act | aaa | aca | cca | 240 |
|---|---|---|---|---|---|---|---|---|---|---|---|---|---|---|---|---|
| Glu | Val | Thr | Gly | Thr | Phe | Asp | Leu | Ile | Ile | Leu | Leu | Thr | Lys | Thr | Pro | |
| 65 |  |  |  | 70 |  |  |  |  | 75 |  |  |  |  | 80 |  |  |

| caa | cta | gac | cgc | atg | tta | aca | gat | att | cag | cct | att | ata | acg | gat | act | 288 |
|---|---|---|---|---|---|---|---|---|---|---|---|---|---|---|---|---|
| Gln | Leu | Asp | Arg | Met | Leu | Thr | Asp | Ile | Gln | Pro | Ile | Ile | Thr | Asp | Thr | |
|  |  |  | 85 |  |  |  |  | 90 |  |  |  |  | 95 |  |  |  |

| aca | aaa | tta | ttg | gta | tta | tca | aac | ggt | ttg | ggt | aat | att | gaa | gtg | atg | 336 |
|---|---|---|---|---|---|---|---|---|---|---|---|---|---|---|---|---|
| Thr | Lys | Leu | Leu | Val | Leu | Ser | Asn | Gly | Leu | Gly | Asn | Ile | Glu | Val | Met | |
|  |  | 100 |  |  |  |  | 105 |  |  |  |  | 110 |  |  |  |  |

| gca | aag | cac | gtg | tca | cgc | cat | caa | att | ttg | gct | ggt | gtc | aca | tta | tgg | 384 |
|---|---|---|---|---|---|---|---|---|---|---|---|---|---|---|---|---|
| Ala | Lys | His | Val | Ser | Arg | His | Gln | Ile | Leu | Ala | Gly | Val | Thr | Leu | Trp | |
|  | 115 |  |  |  |  | 120 |  |  |  |  | 125 |  |  |  |  |  |

| aca | tcg | tca | cta | ata | aag | cca | ggt | gaa | ata | cat | gtt | act | ggt | agt | ggc | 432 |
|---|---|---|---|---|---|---|---|---|---|---|---|---|---|---|---|---|
| Thr | Ser | Ser | Leu | Ile | Lys | Pro | Gly | Glu | Ile | His | Val | Thr | Gly | Ser | Gly | |
| 130 |  |  |  |  | 135 |  |  |  |  | 140 |  |  |  |  |  |  |

| tct | att | aaa | tta | caa | gca | att | ggc | gat | gct | gat | gtc | caa | agt | ata | gcg | 480 |
|---|---|---|---|---|---|---|---|---|---|---|---|---|---|---|---|---|
| Ser | Ile | Lys | Leu | Gln | Ala | Ile | Gly | Asp | Ala | Asp | Val | Gln | Ser | Ile | Ala | |
| 145 |  |  |  | 150 |  |  |  |  | 155 |  |  |  |  | 160 |  |  |

| gat | gct | ttg | aat | cag | gct | ggc | tta | aac | gcc | gaa | att | acc | cca | gat | gtg | 528 |
|---|---|---|---|---|---|---|---|---|---|---|---|---|---|---|---|---|
| Asp | Ala | Leu | Asn | Gln | Ala | Gly | Leu | Asn | Ala | Glu | Ile | Thr | Pro | Asp | Val | |
|  |  |  | 165 |  |  |  |  | 170 |  |  |  |  | 175 |  |  |  |

| atg | aca | gca | att | tgg | cat | aag | gca | ggt | atc | aac | gcg | gtg | ctc | aat | cct | 576 |
|---|---|---|---|---|---|---|---|---|---|---|---|---|---|---|---|---|
| Met | Thr | Ala | Ile | Trp | His | Lys | Ala | Gly | Ile | Asn | Ala | Val | Leu | Asn | Pro | |
|  |  | 180 |  |  |  |  | 185 |  |  |  |  | 190 |  |  |  |  |

| tta | tcc | gtg | ttg | tta | aat | gca | aat | att | gct | gaa | ttt | ggc | aca | gct | ggc | 624 |
|---|---|---|---|---|---|---|---|---|---|---|---|---|---|---|---|---|
| Leu | Ser | Val | Leu | Leu | Asn | Ala | Asn | Ile | Ala | Glu | Phe | Gly | Thr | Ala | Gly | |
|  | 195 |  |  |  |  | 200 |  |  |  |  | 205 |  |  |  |  |  |

| aat | gcc | atg | gat | cta | gca | ttg | aat | att | cta | gat | gag | atg | aag | caa | gtt | 672 |
|---|---|---|---|---|---|---|---|---|---|---|---|---|---|---|---|---|
| Asn | Ala | Met | Asp | Leu | Ala | Leu | Asn | Ile | Leu | Asp | Glu | Met | Lys | Gln | Val | |
| 210 |  |  |  |  | 215 |  |  |  |  | 220 |  |  |  |  |  |  |

| ggt | gcg | tca | caa | ggc | att | aaa | gtt | gac | gtt | agt | ggt | att | atg | acg | gac | 720 |
|---|---|---|---|---|---|---|---|---|---|---|---|---|---|---|---|---|
| Gly | Ala | Ser | Gln | Gly | Ile | Lys | Val | Asp | Val | Ser | Gly | Ile | Met | Thr | Asp | |
| 225 |  |  |  | 230 |  |  |  |  | 235 |  |  |  |  | 240 |  |  |

| ttg | agt | cag | tta | ctt | aaa | cca | gaa | aat | gca | ggt | aat | cat | ttt | ccg | tca | 768 |
|---|---|---|---|---|---|---|---|---|---|---|---|---|---|---|---|---|
| Leu | Ser | Gln | Leu | Leu | Lys | Pro | Glu | Asn | Ala | Gly | Asn | His | Phe | Pro | Ser | |
|  |  |  | 245 |  |  |  |  | 250 |  |  |  |  | 255 |  |  |  |

| atg | tac | caa | gat | att | caa | aat | ggt | aaa | cgt | act | gaa | att | gat | ttc | ttg | 816 |
|---|---|---|---|---|---|---|---|---|---|---|---|---|---|---|---|---|
| Met | Tyr | Gln | Asp | Ile | Gln | Asn | Gly | Lys | Arg | Thr | Glu | Ile | Asp | Phe | Leu | |
|  |  | 260 |  |  |  |  | 265 |  |  |  |  | 270 |  |  |  |  |

| aat | ggt | tac | ttt | gcc | aag | ata | gga | cac | gaa | tct | ggc | att | ccg | acc | cct | 864 |
|---|---|---|---|---|---|---|---|---|---|---|---|---|---|---|---|---|
| Asn | Gly | Tyr | Phe | Ala | Lys | Ile | Gly | His | Glu | Ser | Gly | Ile | Pro | Thr | Pro | |
|  | 275 |  |  |  |  | 280 |  |  |  |  | 285 |  |  |  |  |  |

| ttc | aat | gcc | tta | gtg | aca | cgg | tta | att | cat | gct | aag | gaa | gat | att | gaa | 912 |
|---|---|---|---|---|---|---|---|---|---|---|---|---|---|---|---|---|
| Phe | Asn | Ala | Leu | Val | Thr | Arg | Leu | Ile | His | Ala | Lys | Glu | Asp | Ile | Glu | |
| 290 |  |  |  |  | 295 |  |  |  |  | 300 |  |  |  |  |  |  |

| cgt | gtt | aaa | tta | gca | aaa | cag | caa | gaa | aac | ttt | gaa | att | tga |  |  | 954 |
|---|---|---|---|---|---|---|---|---|---|---|---|---|---|---|---|---|
| Arg | Val | Lys | Leu | Ala | Lys | Gln | Gln | Glu | Asn | Phe | Glu | Ile |  |  |  | |
| 305 |  |  |  | 310 |  |  |  |  | 315 |  |  |  |  |  |  |  |

<210> SEQ ID NO 2
<211> LENGTH: 317
<212> TYPE: PRT
<213> ORGANISM: Leuconostoc mesenteroides

<400> SEQUENCE: 2

Met Lys Ile Ala Ile Ala Gly Phe Gly Ala Leu Gly Ala Arg Leu Gly
1               5                   10                  15

Val Met Leu Gln Ala Gly Gly His Glu Val Thr Gly Ile Asp Gly Trp
            20                  25                  30

Pro Ala His Ile Ala Ala Ile Asn Thr Lys Gly Leu Thr Val Val Lys
        35                  40                  45

Asp Asn Asp Ala Pro Gln Lys Tyr Phe Val Pro Val Met Pro Ala Ser
    50                  55                  60

Glu Val Thr Gly Thr Phe Asp Leu Ile Ile Leu Thr Lys Thr Pro
65                  70                  75                  80

Gln Leu Asp Arg Met Leu Thr Asp Ile Gln Pro Ile Ile Thr Asp Thr
                85                  90                  95

Thr Lys Leu Leu Val Leu Ser Asn Gly Leu Gly Asn Ile Glu Val Met
            100                 105                 110

Ala Lys His Val Ser Arg His Gln Ile Leu Ala Gly Val Thr Leu Trp
        115                 120                 125

Thr Ser Ser Leu Ile Lys Pro Gly Glu Ile His Val Thr Gly Ser Gly
    130                 135                 140

Ser Ile Lys Leu Gln Ala Ile Gly Asp Ala Asp Val Gln Ser Ile Ala
145                 150                 155                 160

Asp Ala Leu Asn Gln Ala Gly Leu Asn Ala Glu Ile Thr Pro Asp Val
                165                 170                 175

Met Thr Ala Ile Trp His Lys Ala Gly Ile Asn Ala Val Leu Asn Pro
            180                 185                 190

Leu Ser Val Leu Leu Asn Ala Asn Ile Ala Glu Phe Gly Thr Ala Gly
        195                 200                 205

Asn Ala Met Asp Leu Ala Leu Asn Ile Leu Asp Glu Met Lys Gln Val
    210                 215                 220

Gly Ala Ser Gln Gly Ile Lys Val Asp Val Ser Gly Ile Met Thr Asp
225                 230                 235                 240

Leu Ser Gln Leu Leu Lys Pro Glu Asn Ala Gly Asn His Phe Pro Ser
                245                 250                 255

Met Tyr Gln Asp Ile Gln Asn Gly Lys Arg Thr Glu Ile Asp Phe Leu
            260                 265                 270

Asn Gly Tyr Phe Ala Lys Ile Gly His Glu Ser Gly Ile Pro Thr Pro
        275                 280                 285

Phe Asn Ala Leu Val Thr Arg Leu Ile His Ala Lys Glu Asp Ile Glu
    290                 295                 300

Arg Val Lys Leu Ala Lys Gln Gln Glu Asn Phe Glu Ile
305                 310                 315

<210> SEQ ID NO 3
<211> LENGTH: 15
<212> TYPE: PRT
<213> ORGANISM: Leuconostoc mesenteroides

<400> SEQUENCE: 3

Met Lys Ile Ala Ile Ala Gly Phe Gly Ala Leu Gly Ala Arg Leu
1               5                   10                  15

-continued

```
<210> SEQ ID NO 4
<211> LENGTH: 10
<212> TYPE: PRT
<213> ORGANISM: Leuconostoc mesenteroides

<400> SEQUENCE: 4

Leu Gly Val Met Leu Gln Ala Gly Gly His
  1               5                  10

<210> SEQ ID NO 5
<211> LENGTH: 10
<212> TYPE: PRT
<213> ORGANISM: Leuconostoc mesenteroides

<400> SEQUENCE: 5

Thr Glu Ile Asp Phe Leu Asn Gly Tyr Phe
  1               5                  10

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Sequence
<220> FEATURE:
<221> NAME/KEY: misc_feature
<222> LOCATION: (27)
<223> OTHER INFORMATION: n indicates any one of a, t, c or g

<400> SEQUENCE: 6
ctgaagctta tgaarathgc hathgcngg                                      29

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Sequence
<220> FEATURE:
<221> NAME/KEY: misc_feature
<222> LOCATION: (30)
<223> OTHER INFORMATION: n indicates any one of a, t, c or g

<400> SEQUENCE: 7
cagaagcttt gdccdccdgc ytgyarcatn ac                                  32

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Sequence
<220> FEATURE:
<221> NAME/KEY: misc_feature
<222> LOCATION: (30)
<223> OTHER INFORMATION: n indicates any one of a, t, c or g

<400> SEQUENCE: 8
ctgaagcttg gygthatgyt dcargchggn gg                                  32

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:Artificially
```

Synthesized Sequence

<400> SEQUENCE: 9
gtcaagcttt adccrttyar raartcdaty tc                               32

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 10
ctgaagctta chgaratyga yttyytdaay gg                               32

<210> SEQ ID NO 11
<211> LENGTH: 785
<212> TYPE: DNA
<213> ORGANISM: Leuconostoc mesenteroides

<400> SEQUENCE: 11
ggatttggtg cacttggtgc acgattaggt gtcatgctcc aggctggtgg ccatgaggtt      60
accgggattg atggttggcc ggcacatatt gctgctatta atacaaaagg tttaacagtc    120
gttaaagata atgatgcacc acaaaagtat tttgtaccag ttatgccggc aagtgaagtg    180
acaggcacat ttgatttaat tattttactc actaaaacac cacaactaga ccgcatgtta    240
acagatattc agcctattat aacggatact acaaaattat tggtattatc aaacggtttg    300
ggtaatattg aagtgatggc aaagcacgtg tcacgccatc aaattttggc tggtgtcaca    360
ttatggacat cgtcactaat aaagccaggt gaaatacatg ttactggtag tggctctatt    420
aaattacaag caattggcga tgctgatgtc caaagtatag cggatgcttt gaatcaggct    480
ggcttaaacg ccgaaattac cccagatgtg atgacagcaa tttggcataa ggcaggtatc    540
aacgcggtgc tcaatccttt atccgtgttg ttaaatgcaa atattgctga atttggcaca    600
gctggcaatg ccatggatct agcattgaat attctagatg agatgaagca agttggtgcg    660
tcacaaggca ttaaagttga cgttagtggt attatgacgg acttgagtca gttacttaaa    720
ccagaaaatg caggtaatca ttttccgtca atgtaccaag atattcaaaa tggtaaacgt    780
actga                                                                785

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 12
tcacttgccg gcataactgg                                                20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 13

```
gtcacaaggc attaaagttg acg                                          23

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 14
gtcgaattct atcatgaaaa ttgcaattgc aggatttggt gcac                   44

<210> SEQ ID NO 15
<211> LENGTH: 58
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 15
gataagctta ctagtattaa atttcaaagt tttcttgctg ttttgctaat ttaacacg    58
```